United States Patent
Liu et al.

(10) Patent No.: US 12,404,244 B2
(45) Date of Patent: Sep. 2, 2025

(54) PAN-KIT KINASE INHIBITOR HAVING QUINOLINE STRUCTURE AND APPLICATION THEREOF

(71) Applicant: Tarapeutics Science Inc., Anhui (CN)

(72) Inventors: Jing Liu, Anhui (CN); Qingsong Liu, Anhui (CN); Yun Wu, Anhui (CN); Beilei Wang, Anhui (CN); ZiPing Q, Anhui (CN); Fengming Zou, Anhui (CN); Qingwang Liu, Anhui (CN); Wenchao Wang, Anhui (CN); Cheng Chen, Anhui (CN); Junjie Wang, Anhui (CN); Li Wang, Anhui (CN)

(73) Assignee: Tarapeutics Science Inc., Anhui (CN)

(*) Notice: Subject to any disclaimer, the term of this patent is extended or adjusted under 35 U.S.C. 154(b) by 1024 days.

(21) Appl. No.: 17/312,667

(22) PCT Filed: Dec. 20, 2018

(86) PCT No.: PCT/CN2018/122307
§ 371 (c)(1),
(2) Date: Jun. 10, 2021

(87) PCT Pub. No.: WO2020/118753
PCT Pub. Date: Jun. 18, 2020

(65) Prior Publication Data
US 2022/0064117 A1     Mar. 3, 2022

(30) Foreign Application Priority Data
Dec. 12, 2018 (CN) .......................... 201811520008.5

(51) Int. Cl.
| | | |
|---|---|---|
| C07D 215/22 | (2006.01) | |
| A61K 31/47 | (2006.01) | |
| A61K 31/4709 | (2006.01) | |
| A61K 31/496 | (2006.01) | |
| A61K 31/5377 | (2006.01) | |
| A61P 35/00 | (2006.01) | |
| C07D 405/12 | (2006.01) | |

(52) U.S. Cl.
CPC ............ *C07D 215/22* (2013.01); *A61K 31/47* (2013.01); *A61K 31/4709* (2013.01); *A61K 31/496* (2013.01); *A61K 31/5377* (2013.01); *A61P 35/00* (2018.01); *C07D 405/12* (2013.01)

(58) Field of Classification Search
None
See application file for complete search history.

(56) References Cited

U.S. PATENT DOCUMENTS 6,143,764 A * 11/2000 Kubo .................. C07D 239/88
                                                                514/252.04
2004/0132727 A1    7/2004   Sakai et al.
2008/0207617 A1    8/2008   Miwa et al.

FOREIGN PATENT DOCUMENTS

| CN | 1344254 A | 4/2002 | |
|---|---|---|---|
| CN | 101248059 A | 8/2008 | |
| CN | 101528702 A | 9/2009 | |
| CN | 103405429 A | 11/2013 | |
| JP | 2007-506777 A | 3/2007 | |
| WO | 96/09294 A1 | 3/1996 | |
| WO | 97/17329 A1 | 5/1997 | |
| WO | 2005/030140 A2 | 4/2005 | |
| WO | 2006/108059 A1 | 10/2006 | |
| WO | WO-2006117567 A2 * | 11/2006 | ............. A61K 47/50 |
| WO | 2009/140549 A1 | 11/2009 | |

OTHER PUBLICATIONS

Meyskens et al., "Cancer prevention: obstacles, challenges, and the road ahead", 2016, J Natl Cancer Inst, 102, pp. 1-8 (Year: 2016).*
Scheltens et al., "Alzheimer's disease", 2016, Seminar, 338, pp. 505-517 (Year: 2016).*
De Strooper et al., "The Cellular Phase of Alzheimer's Disease", 2016, Cell, 164, pp. 603-615 (Year: 2016).*
International Search Report dated Dec. 12, 2019 issued in PCT/CN2018/122307.
International Preliminary Report on Patentability dated Jun. 17, 2021 received in International Application No. PCT/CN2018/122307.

(Continued)

*Primary Examiner* — Jeffrey H Murray
*Assistant Examiner* — Madeline E Braun
(74) *Attorney, Agent, or Firm* — Scully, Scott, Murphy & Presser, P.C.

(57) ABSTRACT

Disclosed are a kinase inhibitor and a pharmaceutical composition comprising the kinase inhibitor. The kinase inhibitor comprises a compound as represented by formula (I) or a pharmaceutically acceptable salt, solvate, ester, acid, metabolite, or prodrug thereof. The compound and composition above can inhibit wild-type KIT and/or mutant KIT tyrosine kinase activity and treat, prevent, or alleviate diseases, disorders, or conditions associated with wild-type KIT and/or mutant KIT kinase activity.

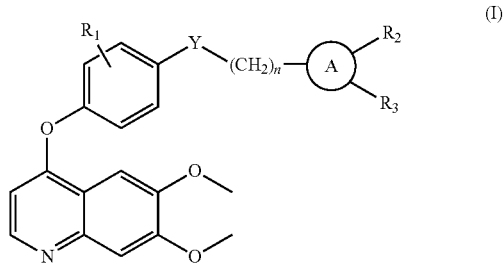

8 Claims, 4 Drawing Sheets

(56) References Cited

OTHER PUBLICATIONS

Kubo K. et al., "Novel Potent Orally Active Selective VEGFR-2 Tyrosine Kinase Inhibitors: Synthesis, Structure-Activity Relationships, and Antitumor Activities of N-Phenyl-N-{4-(4-Quinolyloxy)Phenyl} Ureas", Journal of Medicinal Chemistry 48(5):1359-1366 (2005).
Ple P.A. et al., "Discovery of AZD2932, a New Quinazoline Ether Inhibitor With High Affinity for VEGFR-2 and PDGFR Tyrosine Kinases", Bioorganic & Medicinal Chemistry Letters 22:262-266 (2012).
Wu Y. et al., "Discovery of 2-(4-Chloro-3-(Trifluoromethyl)Phenyl)-N-(4-((6,7-Dimethoxyquinolin-4-yl)Oxyl)Phenyl)Acetamide (CHMFL-KIT-64) as a Novel Orally Available Potent Inhibitor Against Broad-Spectrum Mutants of c-KIT Kinase for Gastrointestinal Stromal Tumors", Journal of Medicinal Chemistry 62:6083-6101 (2019).
Extended European Search Report dated Jul. 20, 2022 received in European Application No. 18 942 754.5.
Abdellateif, M.S., et al., "c-Kit Receptors as a Therapeutic Target in Cancer: Current Insights", OncoTargets and Therapy 2023, pp. 785-799, 16.
Amsterdam, A., et al., "Modulation of c-kit expression in pancreatic adenocarcinoma: A novel stem cell marker responsible for the progression of the disease", Acta Histochemica (2014), pp. 197-203, 116.
Esposito, I., et al., "The Stem Cell Factor—c-kit System and Mast Cells in Human Pancreatic Cancer", Laboratory Investigation, Nov. 2002, pp. 1481-1492, vol. 82, No. 11.
Franceschi, S., et al., "Loss of c-KIT expression in thyroid cancer cells", PLoS One, Received Dec. 22, 2016 Accepted Feb. 28, 2017, Published Mar. 16, 2017, pp. 1-15, e0173913, 12(3).
Kim, D.-J., et al., "Expression and Mutational Analysis of c-kit in Ovarian Surface Epithelial Tumors", J Korean Med Sci 2006, pp. 81-85, 21.
Lin, Z.-H., et al., "A distinct expression pattern and point mutation of c-kit in papillary renal cell carcinomas", Modern Pathology (2004), pp. 611-616, 17.
Linnekin, D., "Early signaling pathways activated by c-Kit in hematopoietic cells", The International Journal of Biochemistry & Cell Biology (1999), pp. 1053-1074, 31.
Naeem, M., et al., "Analysis of c-kit Protein Expression in Small-Cell Lung Carcinoma and Its Implication for Prognosis", Human Pathology, Dec. 2002, pp. 1182-1187, vol. 33, No. 12.
Nakamura, H., et al., "C-kit expression in germinoma: an immunohistochemistry-based study", Journal of Neuro-Oncology (2005), pp. 163-167, 75.
Pathania, S., et al., "A holistic view on c-Kit in cancer: Structure, signaling, pathophysiology and its inhibitors", BBA—Reviews on Cancer 1876 (2021), pp. 1-21, 188631.
Posadas, E.M., et al., "A Prospective Analysis of Imatinib-induced c-KIT Modulation in Ovarian Cancer", A Phase II Clinical Study With Proteomic Profiling, Cancer, Jul. 15, 2007, pp. 309-317, vol. 110, No. 2.
Stankov, K., et al., "C-KIT Signaling in Cancer Treatment", Current Pharmaceutical Design, 2014, pp. 2849-2880, vol. 20, No. 17.
Takeshima, H., et al., "A Review of Soluble c-kit (s-kit) as a Novel Tumor Marker and Possible Molecular Target for the Treatment of CNS Germinoma", Surg Neurol, 2003, pp. 321-325, 60.
Carvajal, R.D., MD., et al., "KIT as a Therapeutic Target in Metastatic Melanoma", JAMA, Jun. 8, 2011, pp. 2327-2334, vol. 305, No. 22.
Carvajal, R.D., et al., "Phase II Study of Nilotinib in Melanoma Harboring KIT Alterations Following Progression to Prior KIT Inhibition", Clin Cancer Res, May 15, 2015, pp. 2289-2296, 21(10).
Hodi, F.S., et al., "Imatinib for Melanomas Harboring Mutationally Activated or Amplified KIT Arising on Mucosal, Acral, and Chronically Sun-Damaged Skin", Journal of Clinical Oncology, Sep. 10, 2013, pp. 3182-3190, vol. 31, No. 26.
Hodi, F.S., et al., "Major response to imatinib mesylate in KIT-mutated melanoma", Journal of Clinical Oncology, 2008, pp. 2046-2051.
Janku, F., et al., "Efficacy and safety of ripretinib in patients with KIT-altered metastatic melanoma", ESMO Open, 2022, pp. 1-10, vol. 7, Issue 4.
Kim, K.H., et al., "A phase II study on the efficacy of regorafenib in treating patients with c-KIT-mutated metastatic malignant melanoma that progressed after previous treatment (KCSG-UN-14-13)", European Journal of Cancer 193 (2023), pp. 1-10, 113312.
Pham, D.M., et al., "KIT and Melanoma: Biological Insights and Clinical Implications", Yonsei Medical Journal., Jul. 2020, pp. 562-571, 61(7).
Quintás-Cardama, A., et al., "Complete response of stage IV anal mucosal melanoma expressing KIT Val560Asp to the multikinase inhibitor sorafenib", Nature Clinical Practice Oncology Dec. 2008, pp. 737-740, vol. 5, No. 12.
Satzger, I., et al., "Anal Mucosal Melanoma with KIT—Activating Mutation and Response to Imatinib Therapy-Case Report and Review of the Literature", Dermatology 2010; pp. 77-81, 220.
Wei, X., et al., "Efficacy Evaluation of Imatinib for the Treatment of Melanoma: Evidence From a Retrospective Study", Oncology Research, Mar. 29, 2019, pp. 495-501, vol. 27.

* cited by examiner

PAN-KIT KINASE INHIBITOR HAVING QUINOLINE STRUCTURE AND APPLICATION THEREOF

TECHNICAL FIELD

The present application relates to KIT kinase inhibitors, especially compounds having an inhibitory activity against wild-type cKIT or various mutants thereof, pharmaceutical compositions containing such compounds, and methods and uses of inhibiting kinase activity using such compounds or compositions.

BACKGROUND OF THE INVENTION

Gastrointestinal stromal tumors (GISTs) are the most common mesenchymal tumor of the gastrointestinal tract. The incidence of GISTs is about 1 in 100,000 to 200,000, accounting for 1-3% of all tumors in the digestive tract. This disease is more common in middle-aged and elderly people, with the median age of onset being 50 to 65 years old. It is rare before 40 years old, but it has also been reported in children. Currently GISTs are considered to be tumors with potentially malignant behavior, and the biological behavior is difficult to predict. GISTs may occur in any part of the digestive tract: most common in stomach (60%~70%), followed by small intestine (20%~30%), less than 10% of an incidence in the esophagus, colon, and rectum, but also seen in the omentum and mesentery.

According to clinical studies, the pathogenesis of gastrointestinal stromal tumors can be divided into three categories based on their genetic molecular profiling: cKIT mutant (80-85%), PDGFRα mutant (5-10%) and cKIT wild-type GISTs (10%). The pathogenesis of gastrointestinal stromal tumors is associated with the activation of the cKIT protein (CD117) signaling pathway. The proto-oncogene cKIT is a homolog of the vKIT gene isolated from the feline fibrosarcoma virus. It is located on human chromosome 4 (4q12-13) with a length of about 90 kb and consisted of 21 exons and 20 introns, and it is highly conserved during evolution. cKIT protein is a receptor tyrosine kinase (RTK) located on cell membrane with a relative molecular mass of 145,000. It is named CD117 according to its cell surface antigenic determinant. cKIT protein belongs to the third type of RTK family and is consisted of five immunoglobulin-like domains (D1~D5), one transmembrane domain, and one cytoplasmic region containing a juxtamembrane domain (JMD) and a tyrosine kinase (TK) domain. The TK domain is further divided into adenosine triphosphate (ATP) domain (TK1) and phosphotransferase domain (TK2). The stem cell factor (SCF) ligand binds to the extracellular domain to form a dimer, leading to autophosphorylation of tyrosine in the TK domain of the cytoplasmic region, further causing autophosphorylation of various downstream effects, and realizing the transmission of various signals. The main signaling pathways include PI3K signaling pathway, JAK-STAT signaling pathway, Ras-Erk signaling pathway, Src family kinase signaling pathway and PLCγ signaling pathway, which ultimately promote proliferation and division of cells and growth and survival of tissues.

Currently surgery, as a traditional surgical therapeutic means, is still the main approach for treatment of gastrointestinal stromal tumors, and the emergence of targeted drugs in recent years has started a new stage in the treatment of GISTs. At present imatinib is a first-line clinical drug for the treatment of gastrointestinal stromal tumors, but generally after two years of administration, nearly 90% of patients will develop drug resistance and suffer from tumor recurrence. The main factor in drug resistance is associated with drug-resistant cKIT kinase mutation. Although currently there are sunitinib as a second-line inhibitor and regorafenib as a third-line inhibitor to clinically overcome the problem caused by drug-resistant cKIT kinase mutation, the clinical responsivity is low and many cKIT mutations were not sensitive to the medicaments. Therefore, there is still a significant demand in clinical for pan-cKIT mutant kinase inhibitors targeting multiple c-KIT targets of gastrointestinal stromal tumors.

SUMMARY OF THE INVENTION

The present invention provides a selective kinase inhibitor, comprising a compound of Formula (I), or a pharmaceutically acceptable salt, solvate, ester, acid, metabolite or prodrug thereof:

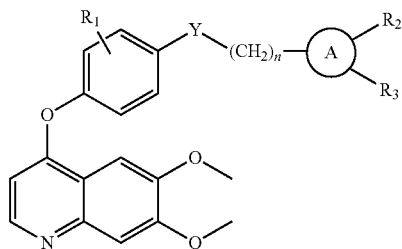

Formula (I)

wherein Y is selected from

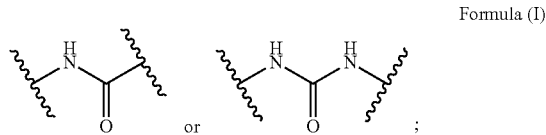 [SMILES: *NC(*)=O ; *NC(=O)N* ; ";" ; "or"]

A is selected from aryl or 6-membered heterocyclyl;
n is an integer selected from 1-3;
$R_1$ is selected from hydrogen, halo, $C_{1-6}$alkyl, $C_{1-6}$haloalkyl, $C_{1-6}$alkoxy and cyano;
each of $R_2$ and $R_3$ is independently selected from hydrogen, halo, $C_{1-6}$alkyl, $C_{1-6}$haloalkyl, $C_{1-6}$alkoxy, or $R_2$ and $R_3$ together form a phenyl or 5-membered heterocyclyl.

In a preferred embodiment, n is preferably 1 when Y is

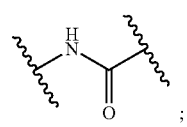 [SMILES: *NC(*)=O ; ";"]

n is preferably 3 when Y is

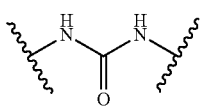

In another aspect, A is preferably selected from phenyl, N-morpholinyl, N-piperidyl or N-piperazinyl. Further preferably, $R_1$ is selected from hydrogen, fluoro, chloro, methyl, ethyl, propyl, or cyano; each of $R_2$ and $R_3$ is independently selected from hydrogen, fluoro, chloro, methyl, ethyl, propyl, trifluoromethyl, difluoromethyl, trifluoroethyl, methoxy, ethoxy, propoxy, or $R_2$ and $R_3$ together form a phenyl or dioxolane.

In a preferred embodiment, the kinase inhibitor of the present invention comprises a compound of Formula (Ia), or a pharmaceutically acceptable salt, solvate, ester, acid, metabolite or prodrug thereof:

Formula (Ia)

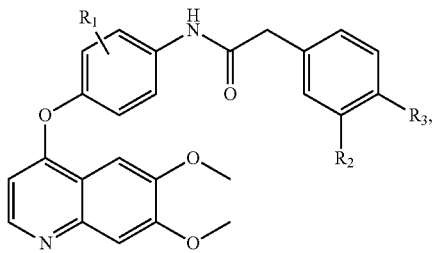

wherein $R_1$, $R_2$ and $R_3$ are defined as above.

More preferably, wherein $R_1$ is selected from hydrogen, fluoro, chloro, and methyl; each of $R_2$ and $R_3$ is independently selected from hydrogen, fluoro, chloro, methyl, and trimethyl, or $R_2$ and $R_3$ together form a phenyl.

In a further preferred embodiment, the kinase inhibitor of the present invention comprises a compound of Formula (Ib), or a pharmaceutically acceptable salt, solvate, ester, acid, metabolite or prodrug thereof:

Formula (Ib)

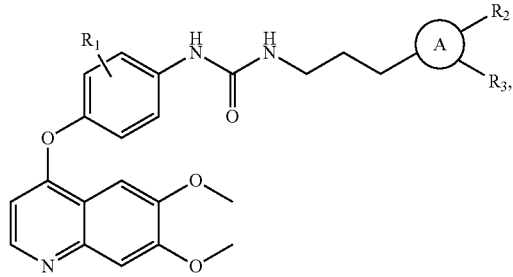

wherein A, $R_1$, $R_2$ and $R_3$ are defined as above.

More preferably, wherein A is selected from phenyl or N-morpholinyl; $R_1$ is hydrogen; each of $R_2$ and $R_3$ is independently selected from hydrogen, fluoro, chloro, methyl and trifluoromethyl.

The present invention further relates to a pharmaceutical composition comprising the above compound or a pharmaceutically acceptable salt, solvate, ester, acid, metabolite or prodrug thereof, a method and a use of the above compound or pharmaceutical composition for inhibiting tyrosine kinase (wild-type KIT and/or mutant KIT) activity, as well as a method and a use thereof for treatment, prevention or amelioration of diseases, disorders or conditions that are modulated or otherwise affected by kinase activity of wild-type KIT and/or mutant KIT or in which kinase activity of wild-type KIT and/or mutant KIT is implicated.

DETAILED DESCRIPTION OF THE INVENTION

Terminology

Figure 1A:
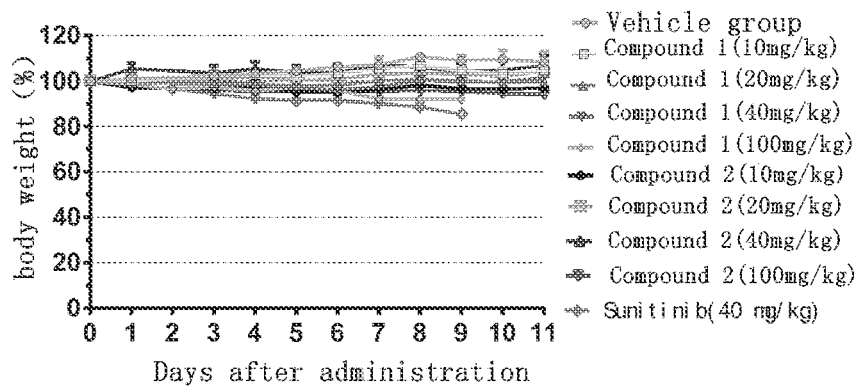
FIGS. 1a-1c show the tumor inhibitory effects of Compound 1 and Compound 2 in a tumor-grafted mouse model established with tel-cKIT/T670I-BaF3 cells.

Unless defined otherwise, all technical and scientific terms used herein have the same meaning as is commonly understood by one of skill in the art to which the claimed subject matter belongs.

Unless otherwise indicated, conventional methods of mass spectroscopy, NMR, HPLC, protein chemistry, biochemistry, recombinant DNA techniques and pharmacology, within the skill of the art are employed in the invention. Unless specific definitions are provided, the nomenclature employed in connection with, and the laboratory procedures and techniques of, analytical chemistry, synthetic organic chemistry, and medicinal and pharmaceutical chemistry described herein are those known in the art. The foregoing techniques and procedures can be generally performed of conventional methods well known in the art and as described in various general and more specific references that are cited and discussed throughout the present specification.

The term "alkyl" refers to an aliphatic hydrocarbon group, which may have branched or straight chain. Depending on the structure, an alkyl group can be a monoradical or a diradical (i.e., an alkylene group). In the invention, the alkyl group is preferably an alkyl having 1 to 8 carbon atoms, more preferably a "lower alkyl" having 1 to 6 carbon atoms, and even more preferably an alkyl having 1 to 4 carbon atoms. Typical alkyl groups include, but are not limited to, methyl, ethyl, propyl, butyl, pentyl, hexyl, and the like. It should be understood that the "alkyl" as mentioned herein encompasses all configurations and conformations that may exist of the alkyl, e.g., the "propyl" as mentioned herein intends to encompass n-propyl and isopropyl, the "butyl" encompasses n-butyl, isobutyl, and tertiary butyl, the "pentyl" encompasses n-pentyl, isopentyl, neopentyl, tert-pentyl, and pent-3-yl.

The term "alkoxy" refers to a —O-alkyl group, where alkyl is as defined herein. Typical alkoxy groups include, but are not limited to, methoxy, ethoxy, propoxy, butoxy, pentyloxy, hexyloxy, and the like.

The term "cycloalkyl" refers to a monocyclic or polycyclic radical that contains only carbon and hydrogen. Cycloalkyl groups include groups having from 3 to 12 ring atoms. Depending on the structure, a cycloalkyl group can be a monoradical or a diradical (e.g., a cycloalkylene group). In the invention, the cycloalkyl group is preferably a cycloalkyl having 3 to 8 carbon atoms, and more preferably a "lower cycloalkyl" having 3 to 6 carbon atoms. Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, and adamantyl.

The term "aromatic" refers to a planar ring having a delocalized π-electron system containing 4n+2 π electrons, where n is an integer. Aromatic rings can be formed by five, six, seven, eight, nine, or more than nine atoms. Aromatics can be optionally substituted. The term "aromatic" includes both carbocyclic aryl (e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical (i.e., an arylene group).

The term "aryloxy" refers to —O-aryl, wherein aryl is as defined herein.

The term "heteroaryl" refers to an aryl group that includes one or more ring heteroatoms selected from nitrogen, oxygen and sulfur. An N-containing "heteroaryl" moiety refers to an aromatic group in which at least one of the skeletal atoms of the ring is a nitrogen atom. Depending on the structure, the heteroaryl group may be a monoradical or a diradical (i.e., a heteroarylene group). Examples of heteroaryl groups include, but are not limited to pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, indazolyl, indolizinyl, phthalazinyl, pyridazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, naphthyridinyl, furopyridinyl, and the like.

As used herein, the term "heteroalkyl" refers to an alkyl radical, as defined herein, in which one or more skeletal chain atoms is a heteroatom, e.g., oxygen, nitrogen, sulfur, silicon, phosphorus or combinations thereof. The heteroatom(s) may be placed at any interior position of the heteroalkyl group or at the position at which the heteroalkyl group is attached to the remainder of the molecule.

As used herein, the term "heterocycloalkyl" or "heterocyclyl" refers to a non-aromatic ring wherein one or more atoms forming the ring is a heteroatom selected from the group consisting of nitrogen, oxygen and sulfur. Heterocycloalkyl rings can be formed by three, four, five, six, seven, eight, nine, or more than nine atoms. Heterocycloalkyl rings can be optionally substituted. Examples of heterocycloalkyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, imidazolidine, pyrrolidone, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Depending on the structure, a heterocycloalkyl group can be a monoradical or a diradical (i.e., a heterocycloalkylene group).

The term "halo" or "halogen" means fluoro, chloro, bromo and iodo.

The terms "haloalkyl", "haloalkoxy" and "haloheteroalkyl" include alkyl, alkoxy or heteroalkyl structures in which at least one hydrogen is replaced with a halogen atom. In certain embodiments in which two or more hydrogen atoms are replaced with halogen atoms, the halogen atoms are the same or different as one another.

The term "hydroxy" refers to an —OH group.

The term "cyano" refers to a —CN group.

The term "ester group" refers to a chemical moiety of the formula —COOR, wherein R is selected from alkyl, cycloalkyl, aryl, heteroaryl (connected via a ring carbon) and heterocyclyl (connected via a ring carbon).

The term "amino" refers to an —NH$_2$ group.

The term "aminoacyl" refers to a —CO—NH$_2$ group.

The term "amide" or "acylamino" refers to —NR—CO—R', wherein R and R' is respectively independently hydrogen or alkyl.

The term "optionally" means that the subsequently described event(s) may occur or may not occur, and includes both event(s), which occur, and events that do not occur. The term "optionally substituted" or "substituted" means that the referenced group may be substituted with one or more additional group(s) individually and independently selected from the group consisting of the group consisting of alkyl, cycloalkyl, aryl, heteroaryl, heterocyclyl, hydroxy, alkoxy, cyano, halo, amide, nitro, haloalkyl, amino, mesyl, alkylcarbonyl, alkoxycarbonyl, heteroarylalkyl, heterocycloalkylalkyl, aminoacyl, amino-protecting group and the like. Wherein, the amino-protecting group is preferably selected from pivaloyl, tert-butoxycarbonyl, benzyloxycarbonyl, 9-fluorenylmethoxycarbonyl, benzyl, p-methoxybenzyl, allyloxycarbonyl, and trifluoroacetyl, etc.

The term "tyrosine protein kinase (TPK)" as used herein is a type of kinases that catalyze the transfer of the y-phosphate from adenosine triphosphate (ATP) to tyrosine residue on proteins and that is capable of catalyzing the phosphorylation of tyrosine residue of various protein substrates, and thus has an important effect in cell growth, proliferation and differentiation.

The terms "inhibits", "inhibiting", or "inhibitor" of a kinase, as used herein, refer to inhibition of phosphotransferase activity.

A "metabolite" of a compound disclosed herein is a derivative of that compound that is formed when the compound is metabolized. The term "active metabolite" refers to a biologically active derivative of a compound that is formed when the compound is metabolized. The term "metabolized" as used herein, refers to the sum of the processes (including, but not limited to, hydrolysis reactions and reactions catalyzed by enzymes, such as, oxidation reactions) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic acid molecule to aromatic alcohol, aliphatic alcohol, carboxylic acid, amine and free sulfhydryl group. Further information on metabolism may be obtained from *The Pharmacological Basis of Therapeutics,* 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, metabolites of a compound are formed by oxidative processes and correspond to the corresponding hydroxy-containing compound. In some embodiments, a compound is metabolized to pharmacologically active metabolites. The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

As used herein, the term "target protein" refers to a protein molecule or a portion of a protein capable of being bound by a selective binding compound. In certain embodiments, a target protein is a tyrosine kinase KIT (wild-type, or various mutants or the combination thereof), ABL (wild-type, or various mutants or the combination thereof), EGFR (wild-type, or various mutants or the combination thereof), FLT3 (wild-type, or various mutants or the combination thereof), VEGFR2 (wild-type, or various mutants or the combination thereof), RET (wild-type, or various mutants or the combination thereof), PDGFRα (wild-type, or various mutants or the combination thereof), PDGFRβ (wild-type, or various mutants or the combination thereof), FGFR1 (wild-type, or various mutants or the combination thereof), FGFR2 (wild-type, or various mutants or the combination thereof), FGFR3 (wild-type, or various mutants or the combination thereof), FGFR4 (wild-type, or various mutants or the combination thereof).

$IC_{50}$ as used herein refers to an amount, concentration or dosage of a particular test compound that achieves a 50% inhibition of a maximal response, in an assay that measures such response.

$EC_{50}$ as used herein refers to a dosage, concentration or amount of a test compound that elicits a dose-dependent response at 50% of maximal expression of a particular response that is induced, provoked or potentiated by the particular test compound.

The $GI_{50}$ as used herein refers to a concentration of a medicament that is necessary for inhibiting 50% of cell proliferation, i.e., the medicament concentration at which the growth of cells such as cancer cells is inhibited or controlled by 50%.

Novel Kinase Inhibitor of the Present Invention

The present invention provides a selective kinase inhibitor, comprising a compound of Formula (I) or a pharmaceutically acceptable salt, solvate, ester, acid, metabolite or prodrug thereof:

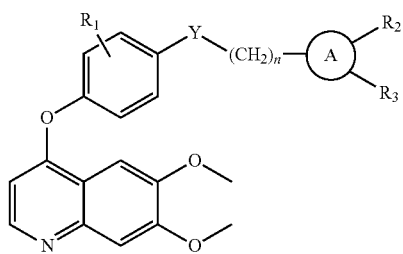

wherein Y is selected from

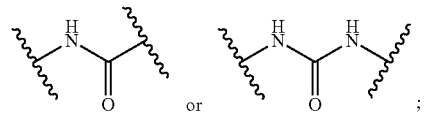

Formula (I)

A is selected from aryl or 6-membered heterocyclyl;
n is an integer selected from 1-3;
$R_1$ is selected from hydrogen, halo, $C_{1-6}$alkyl, $C_{1-6}$haloalkyl, $C_{1-6}$alkoxy and cyano;
each of $R_2$ and $R_3$ is independently selected from hydrogen, halo, $C_{1-6}$alkyl, $C_{1-6}$haloalkyl, $C_{1-6}$alkoxy, or $R_2$ and $R_3$ together form a phenyl or 5-membered heterocyclyl.

In a preferred embodiment, n is preferably 1 when Y is

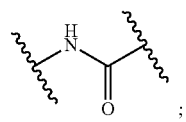 [SMILES: *NC(*)=O ; ";"]

n is preferably 3 when Y is

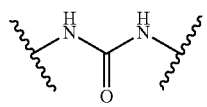

In another aspect, A is preferably selected from phenyl, N-morpholinyl, N-piperidyl or N-piperazinyl. Further preferably, $R_1$ is selected from hydrogen, fluoro, chloro, methyl, ethyl, propyl, or cyano; each of $R_2$ and $R_3$ is independently selected from hydrogen, fluoro, chloro, methyl, ethyl, propyl, trifluoromethyl, difluoromethyl, trifluoroethyl, methoxy, ethoxy, propoxy, or $R_2$ and $R_3$ together form a phenyl or dioxolane.

In a preferred embodiment, the kinase inhibitor of the present invention comprises a compound of Formula (Ia), or a pharmaceutically acceptable salt, solvate, ester, acid, metabolite or prodrug thereof:

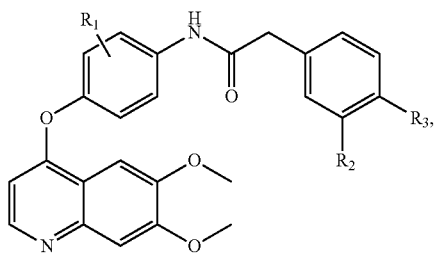

Formula (Ia)

wherein $R_1$, $R_2$ and $R_3$ are defined as above.

More preferably, wherein $R_1$ is selected from hydrogen, fluoro, chloro, and methyl; each of $R_2$ and $R_3$ is independently selected from hydrogen, fluoro, chloro, methyl, and trimethyl, or $R_2$ and $R_3$ together form a phenyl.

In a further preferred embodiment, the kinase inhibitor of the present invention comprises a compound of Formula (Ib), or a pharmaceutically acceptable salt, solvate, ester, acid, metabolite or prodrug thereof:

Formula (Ib)

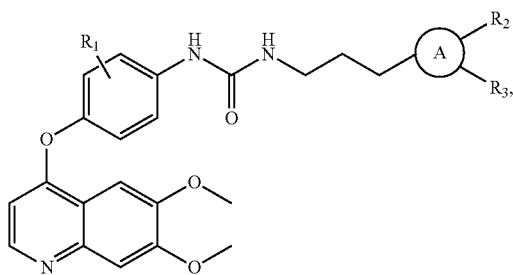

wherein A, $R_1$, $R_2$ and $R_3$ are defined as above.

More preferably, wherein A is selected from phenyl or N-morpholinyl; $R_1$ is hydrogen; each of $R_2$ and $R_3$ is independently selected from hydrogen, fluoro, chloro, methyl and trifluoromethyl.

In a preferred embodiment, the kinase inhibitor of the present invention comprises a compound of Table 1 as below or a pharmaceutically acceptable salt, solvate, ester, acid, metabolite or prodrug thereof.

TABLE 1

| No. | Structure of Compound |
|---|---|
| 1 | 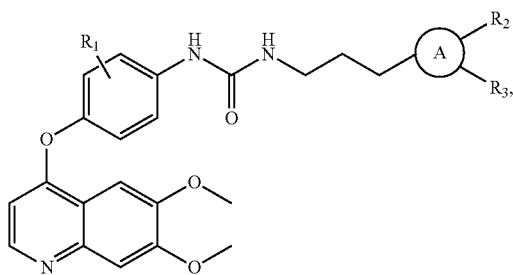 |
| 2 | 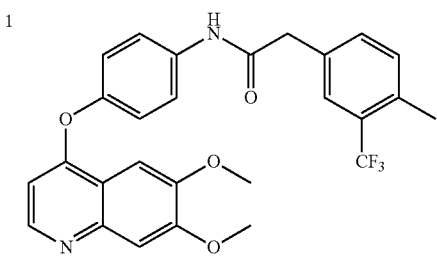 |
| 3 | 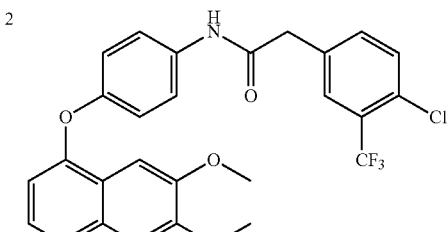 |

TABLE 1-continued

| No. | Structure of Compound |
|---|---|
| 4 | 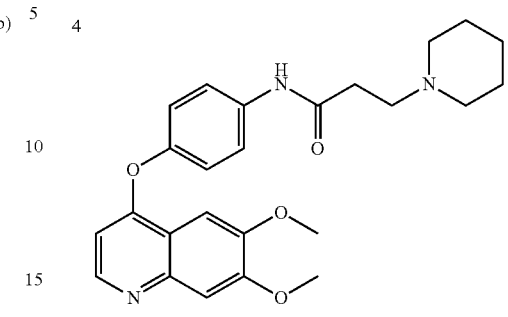 |
| 5 | 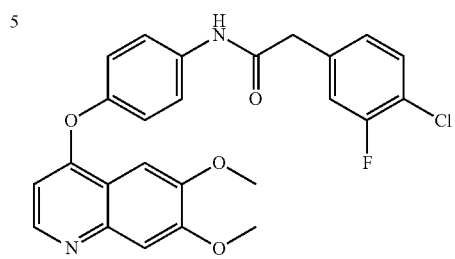 |
| 6 | 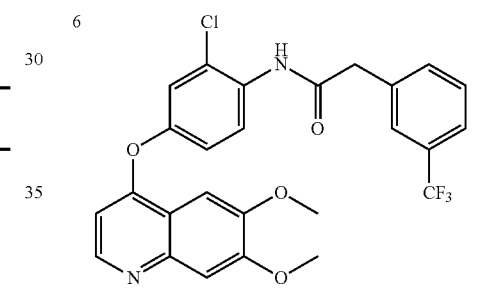 |
| 7 | 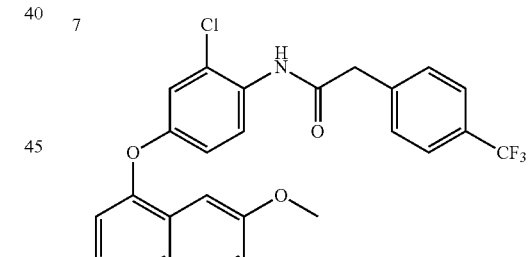 |
| 8 | 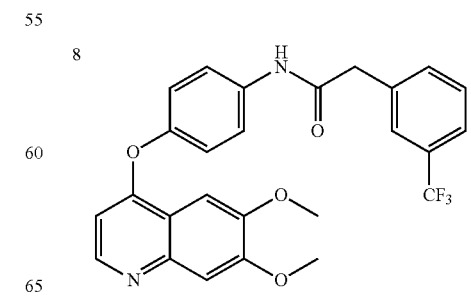 |

TABLE 1-continued
| No. | Structure of Compound |
|---|---|
| 9 | 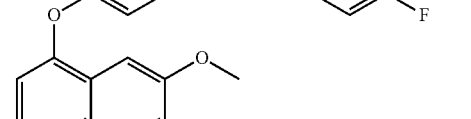 |
| 10 | 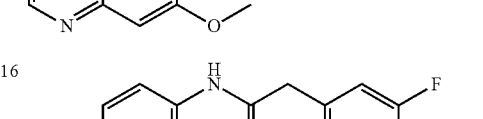 |
| 11 | 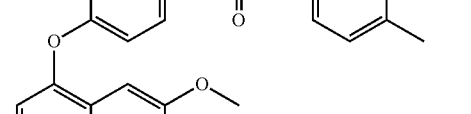 |
| 12 | 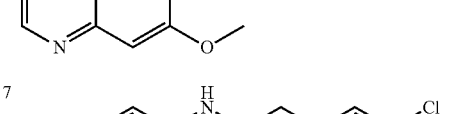 |
| 13 | 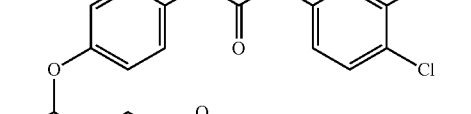 |
| 14 | 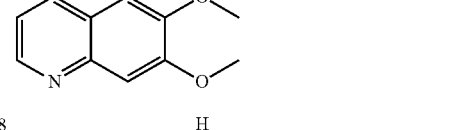 |
| 15 | 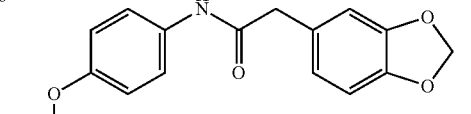 |
| 16 | 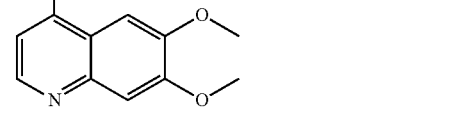 |
| 17 | 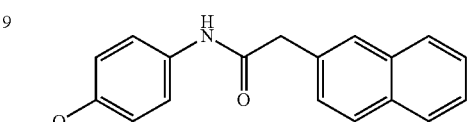 |
| 18 | 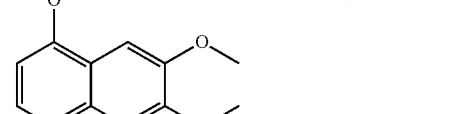 |
| 19 | 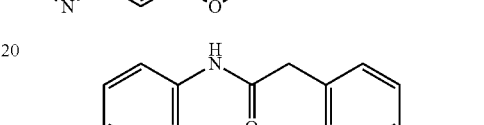 |
| 20 | 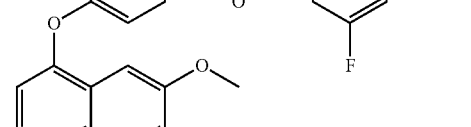 |

TABLE 1-continued
| No. | Structure of Compound |
|---|---|
| 21 | 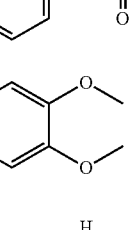 |
| 22 | |
| 23 | |
| 24 | |
| 25 | |
| 26 | |
| 27 | |
| 28 | |
| 29 | |
| 30 | |

TABLE 1-continued

| No. | Structure of Compound |
|---|---|
| 31 | 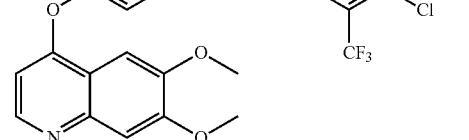 |
| 32 | |
| 33 | |
| 34 | |
| 35 | |
| 36 | 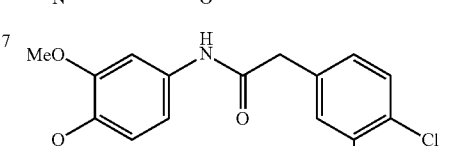 |
| 37 | |
| 38 | |
| 39 | |
| 40 | |

Any combination of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

Described herein are novel kinase inhibitors. The pharmaceutically acceptable salts, solvates, esters, acids, pharmaceutically active metabolites and prodrugs of these compounds are also described herein.

In additional or further embodiments, the compounds described herein are metabolized upon administration to an organism in need to produce a metabolite that is then used to produce a desired effect, including a desired therapeutic effect.

Compounds described herein may be formed as, and/or used as, pharmaceutically acceptable salts. The type of pharmaceutical acceptable salts, include, but are not limited to: (1) acid-addition salts, formed by reacting the free base form of the compound with a pharmaceutically acceptable inorganic acid such as hydrochloric acid, hydrobromic acid, sulfuric acid, nitric acid, phosphoric acid, metaphosphoric acid, and the like; or with an organic acid such as acetic acid, propionic acid, hexanoic acid, cyclopentanepropionic acid, glycolic acid, pyruvic acid, lactic acid, malonic acid, malic acid, citric acid, succinic acid, maleic acid, tartaric acid, fumaric acid, trifluoroacetic acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 4-methylbicyclo-[2.2.2]oct-2-ene-1-carboxylic acid, 2-naphthalenesulfonic acid, tertiary butylacetic acid, glucoheptonic acid, 4,4'-methylenebis-(3-hydroxy-2-ene-1-carboxylic acid), 3-phenylpropionic acid, trimethylacetic acid, lauryl sulfuric acid, gluconic acid, glutamic acid, salicylic acid, hydroxynaphthoic acid, stearic acid, muconic acid, and the like; (2) base-addition salts formed when an acidic proton present in the parent compound either is replaced by a metal ion, e.g., an alkali metal ion (e.g. lithium, sodium, potassium), an alkaline earth ion (e.g. magnesium, or calcium), or an aluminum ion; or coordinates with an organic base or an inorganic base. Acceptable organic bases include ethanolamine, diethanolamine, triethanolamine, trimethylamine, N-methylglucamine, and the like. Acceptable inorganic bases include aluminum hydroxide, calcium hydroxide, potassium hydroxide, sodium carbonate, sodium hydroxide, and the like.

The corresponding counterions of the pharmaceutically acceptable salts may be analyzed and identified using various methods including, but not limited to, ion exchange chromatography, ion chromatography, capillary electrophoresis, inductively coupled plasma, atomic absorption spectroscopy, mass spectrometry, or any combination thereof.

The salts are recovered by using at least one of the following techniques: filtration, precipitation with a nonsolvent followed by filtration, evaporation of the solvent, or, in the case of aqueous solutions, lyophilization.

The screening and characterization of the pharmaceutically acceptable salts, polymorphs and/or solvates may be accomplished using a variety of techniques including, but not limited to, thermal analysis, x-ray diffraction, spectroscopy, microscopy, and elemental analysis. The various spectroscopic techniques used include, but are not limited to, Raman, FTIR, UVIS, and NMR (liquid and solid state). The various microscopy techniques include, but are not limited to, IR microscopy and Raman microscopy.

The Pharmaceutical Composition of the Present Invention

The present application also provides a pharmaceutical composition comprising at least one compound of Formula (I), or a pharmaceutically acceptable salt, solvate, ester, acid, pharmaceutically active metabolite or prodrug of said compound, and a pharmaceutically acceptable carrier or excipient, and optionally other therapeutic agents.

In the course of treatment, it may be used alone or in combination with one or more other therapeutic agents according to the situation. The medicament comprising a compound of the invention may be administered to a patient through at least one of injection, oral, inhalation, rectal and transdermal administration. Other therapeutic agents may be selected from the following: immunosuppressants (e.g., tacrolimus, cyclosporin, rapamycin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, fluoxyprednisolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), allergy vaccines, antihistamines, antileukotrienes, p-agonists, theophylline, anticholinergics, or other selective kinase inhibitors (e.g., mTOR inhibitors, c-Met inhibitors) or her2 antibodies. In addition, the other therapeutic agents may also be Rapamycin, Crizotinib, Tamoxifen, Raloxifene, Anastrozole, Exemestane, Letrozole, Herceptin™ (Trastuzumab), Gleevec™ (Imatinib), Taxol™ (Paclitaxel), Cyclophosphamide, Lovastatin, Minosine, Cytarabine, 5-Fluorouracil (5-FU), Methotrexate (MTX), Taxotere™ (Docetaxel), Zoladex™ (Goserelin), Vincristine, Vinblastine, Nocodazole, Teniposide, Etoposide, Gemzar™ (Gemcitabine), Epothilone, Navelbine, Camptothecin, Daunonibicin, Dactinomycin, Mitoxantrone, Amsacrine, Doxorubicin (Adriamycin), Epirubicin or Idarubicin. Alternatively, other therapeutic agents may be cytokines such as G-CSF (Granulocyte-Colony Stimulating Factor). Alternatively, other therapeutic agents may be, CMF (Cyclophosphamide, Methotrexate and 5-Fluorouracil), CAF (Cyclophosphamide, Adriamycin and 5-Fluorouracil), AC (Adriamycin and Cyclophosphamide), FEC (5-Fluorouracil, Epirubicin and Cyclophosphamide), ACT or ATC (Adriamycin, Cyclophosphamide and Paclitaxel) or CMFP (Cyclophosphamide, Methotrexate, 5-Fluorouracil and Prednisone).

In the embodiments of the invention, when a patient is treated in accordance with the invention, the amount of a given agent will vary depending upon factors such as the particular dosing regimen, the type of the disease or condition and its severity, the identity (e.g., weight) of the subject or host in need of treatment, but can be routinely determined in a manner known in the art according to the particular circumstances surrounding the case, including, e.g., the specific agent being administered, the route of administration, the condition being treated, and the subject or host being treated. In general, doses employed for adult human treatment will typically be in the range of 0.02-5000 mg per day, such as from about 1-1500 mg per day. The desired dose may conveniently be presented in a single dose or as divided doses administered simultaneously (or over a short period of time) or at appropriate intervals, for example as two, three, four or more sub-doses per day. It will be appreciated by those skilled in the art that, although the above dosage ranges are given, the specific effective amounts may be appropriately adjusted depending on the condition of the patient and the judgment of the practitioner.

Use of the Pharmaceuticals of the Present Invention

The compound of formula (I), or a pharmaceutically acceptable salt, solvate, ester, acid, metabolite or prodrug thereof, or a pharmaceutical composition comprising the same may be used for inhibiting the activity of tyrosine kinase KIT (wild-type or various mutants or the combination thereof). The compound of formula (I), or a pharmaceutically acceptable salt, solvate, ester, acid, metabolite or prodrug thereof, or a pharmaceutical composition thereof may be used for the treatment, prevention or amelioration of one or more diseases selected from the group consisting of: solid tumors (including benign or especially malignant types), especially sarcoma, Gastrointestinal Stromal Tumor (GIST), colorectal cancer, Acute Myeloblastic Leukemia (AML), Chronic Myelogenous Leukemia (CML), neoplasia, thyroid carcinoma, systemic mastocytosis, eosinophilia syndrome, fibrosis, lupus erythematosus, graft versus host disease, neurofibromatosis, pulmonary hypertension, Alzheimer's disease, seminoma, dysgerminoma, mast cell tumors, lung cancer, bronchial carcinoma, testicular intraepithelial neoplasia, melanoma, breast cancer, neuroblastoma, papillary/follicular thyroid carcinoma, malignant lymphoma, non-Hodgkin's lymphoma, multiple endocrine neoplasia type 2, pheochromocytoma, thyroid carcinoma, parathyroid hyperplasia/adenoma, colon cancer, colorectal adenoma, ovarian cancer, prostate cancer, glioblastoma, brain tumor, malignant glioma, pancreatic cancer, malignant pleural endothelioma, hemangioblastoma, hemangioma, kidney cancer, liver cancer, adrenal carcinoma, bladder cancer, stomach cancer, rectal cancer, vaginal cancer, cervical cancer, endometrial cancer, multiple myeloma, neck and head tumors, as well as other proliferative conditions, or the like, or the combination thereof. It is especially preferred for the treatment of Gastrointestinal Stromal Tumor (GIST), colorectal cancer, Acute Myeloblastic Leukemia (AML), Chronic Myelogenous Leukemia (CML), thyroid carcinoma, or the like, or the combination thereof.

The compound of formula (I), or a pharmaceutically acceptable salt, solvate, ester, acid, metabolite or prodrug thereof, or a pharmaceutical composition thereof may be used for the treatment, prevention or amelioration of autoimmune diseases selected from the group consisting of: arthritis, rheumatic arthritis, osteoarthritis, lupus, rheumatoid arthritis, inflammatory bowel disease, psoriatic arthritis, osteoarthritis, Still's disease, Juvenile arthritis, diabetes, myasthenia gravis, Hashimoto's thyroiditis, Ord's hyroiditis, Graves' disease, Sjögren's syndrome, multiple sclerosis, Guillain-Barré syndrome, acute disseminated encephalomyelitis, Addison's disease, Opsoclonus-Myoclonus-Ataxia, ankylosing spondylitis, antiphospholipid syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm-type autoimmune hemolytic anemia, Wegener's granulomatosis, psoriasis, alopecia universalis, Behcet's disease, chronic fatigue, Familial dysautonomia, endometriosis, interstitial cystitis, neuromyotonia, scleroderma, vulvodynia or combination thereof.

The compound of formula (I), or a pharmaceutically acceptable salt, solvate, ester, acid, metabolite or prodrug thereof, or a pharmaceutical composition thereof may be preferably used for the treatment, prevention or amelioration of the following hematological malignancies: myeloma, acute lymphocytic leukemia, acute myeloblastic leukemia, acute promyelocytic leukemia, chronic lymphocytic leukemia, chronic myeloblastic leukemia, chronic neutrophilic leukemia, acute undifferentiated leukemia, anaplastic large-cell lymphoma, adult T-cell acute lymphoblastic leukemia, acute myeloblastic leukemia with trilineage myelodysplasia, mixed lineage leukemia, myelodysplasia syndromes, myeloproliferative disorders, multiple myeloma, myeloid sarcoma or a combination thereof.

The present invention is more preferably useful in treating, preventing or ameliorating gastrointestinal stromal tumor, especially gastrointestinal stromal tumor associated with KIT mutation, more particularly gastrointestinal stromal tumor that is resistant to Imatinib and/or Suntinib caused by KIT mutation.

Preparation of the Compounds

Compounds of formula (I) may be synthesized using standard synthetic techniques known to those of skill in the art or using methods known in the art in combination with methods described herein. In additions, solvents, temperatures and other reaction conditions presented herein may vary according to those of skill in the art. As a further guide the following synthetic methods may also be utilized.

The reactions can be employed in order to provide the compounds described herein or they may be used to synthesize fragments which are subsequently joined by the methods described herein and/or known in the art.

In certain embodiments, provided herein are methods of making and methods of using tyrosine kinase inhibitor compounds described herein. In certain embodiments, compounds described herein can be synthesized using the following synthetic schemes. Compounds may be synthesized using methodologies analogous to those described below by the use of appropriate alternative starting materials.

The starring materials used for the synthesis of the compounds described herein may be synthesized or can be obtained from commercial sources. The compounds described herein and other related compounds having different substituents can be synthesized using techniques and materials known to those of skill in the art. General methods for the preparation of compounds as disclosed herein may be derived from known reactions in the field, and the reactions may be modified by the use of appropriate reagents and conditions, as would be recognized by the skilled person, for the introduction of the various moieties into the molecules as provided herein.

The products of the reactions may be isolated and purified, if desired, using conventional techniques, including, but not limited to, filtration, distillation, crystallization, chromatography and the like. Such products may be characterized using conventional means, including physical constants and spectral data.

A non-limiting example of a synthetic approach for the preparation of a compound of formula (I) is shown in the following synthetic route.

Example 1: N-(4-(((6,7-dimethoxyquinolin-4-yl)oxy)phenyl)-2-(4-methyl-3-(trifluoromethyl)phenyl)acetamide

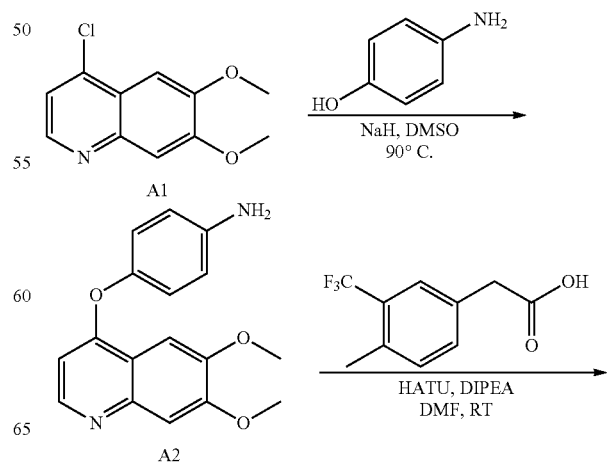

-continued

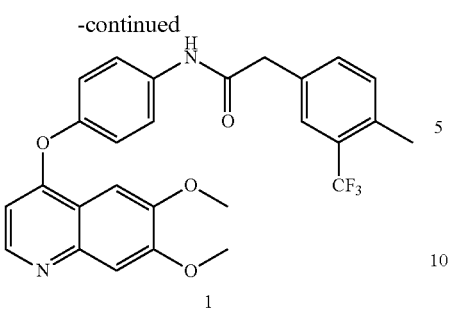

1

4-((6,7-dimethoxyquinolin-4-yl)oxy)phenylamine (A2): to a round-bottom flask was added 4-hydroxyphenylamine (2.0 g), followed by dimethyl sulfoxide (30 ml), and then by addition of sodium hydride (807 mg) dropwise in an ice bath. The reaction system was stirred for 30 min at room temperature. Next, 4-chloro-6,7-dimethoxyquinoline (4.1 g) was added, and the reaction system was allowed to react overnight at 90° C. After completion of the reaction, the system was added with water and filtered, with the solids subjected to washing with water and a small amount of methanol. The resultant brown solids were used directly in the next step.

N-(4-((6,7-dimethoxyquinolin-4-yl)oxy)phenyl)-2-(4-methyl-3-(trifluoromethyl)phenyl)acetamide (1): to a round-bottom flask was added 4-((6,7-dimethoxyquinolin-4-yl)oxy)phenylamine (1 g), followed by N,N-dimethylformamide (10 ml), HATU (1.92 g), 4-methyl-3-trifluoromethylphenylacetic acid (1.10 g) and N,N-diisopropylethylamine (0.87 g). The reaction system was stirred overnight at room temperature. After completion of the reaction, the system was added with water and extracted with ethyl acetate, with the organic phase subjected to drying over anhydrous sodium sulfate. The organic phase was filtered, the solvent was removed from the filtrate under reduced pressure, and the residue was purified via pressurized silica gel column chromatography to obtain the Compound 1. LC/MS: M+H 497.1.

Example 2: N-(4-((6,7-dimethoxyquinolin-4-yl)oxy)phenyl)-2-(4-chloro-3-(trifluoromethyl)phenyl)-acetamide

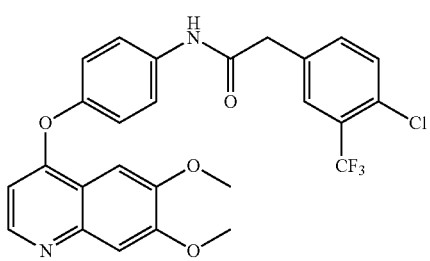

Synthesis of the compound of Example 2 was completed by using procedures similar to those of Example 1. MS(ESI) m/z(M+1)+: 517.11.

Example 3: N-(4-((6,7-dimethoxyquinolin-4-yl)oxy)phenyl)-2-phenylacetamide

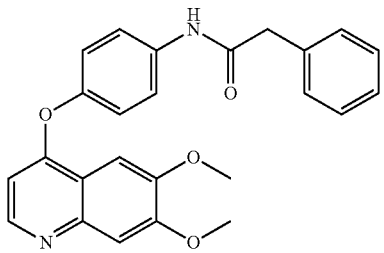 [SMILES: COc1cc2nccc(Oc3ccc(NC(=O)Cc4ccccc4)cc3)c2cc1OC]

Synthesis of the compound of Example 3 was completed by using procedures similar to those of Example 1. MS(ESI) m/z(M+1)+: 415.16.

Example 4: N-(4-((6,7-dimethoxyquinolin-4-yl)oxy)phenyl)-3-(piperidin-1-yl)propanamide

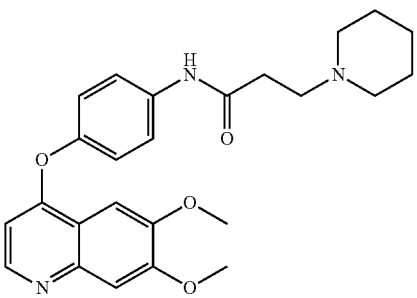 [SMILES: COc1cc2nccc(Oc3ccc(NC(=O)CCN4CCCCC4)cc3)c2cc1OC]

Synthesis of the compound of Example 4 was completed by using procedures similar to those of Example 1. MS(ESI) m/z(M+1)+: 436.22.

Example 5: N-(4-((6,7-dimethoxyquinolin-4-yl)oxy)phenyl)-2-(4-chloro-3-fluorophenyl)acetamide

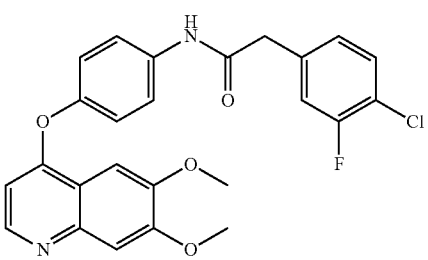 [SMILES: COc1cc2nccc(Oc3ccc(NC(=O)Cc4ccc(Cl)c(F)c4)cc3)c2cc1OC]

Synthesis of the compound of Example 5 was completed by using procedures similar to those of Example 1. MS(ESI) m/z(M+1)+: 467.11.

Example 6: N-(2-chloro-4-((6,7-dimethoxyquinolin-4-yl)oxy)phenyl)-2-(3-(trifluoromethyl)phenyl)acetamide

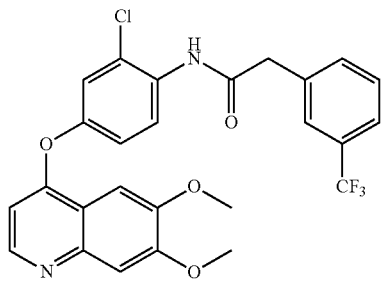 [SMILES: COc1cc2nccc(Oc3ccc(NC(=O)Cc4cccc(C(F)(F)F)c4)c(Cl)c3)c2cc1OC]

Synthesis of the compound of Example 6 was completed by using procedures similar to those of Example 1. MS(ESI) m/z(M+1)+: 517.11.

Example 7: N-(2-chloro-4-((6,7-dimethoxyquinolin-4-yl)oxy)phenyl)-2-(4-(trifluoromethyl)phenyl)acetamide

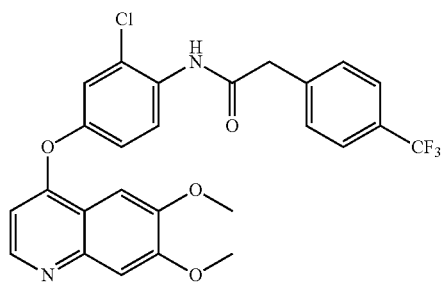 [SMILES: COc1cc2nccc(Oc3ccc(NC(=O)Cc4ccc(C(F)(F)F)cc4)c(Cl)c3)c2cc1OC]

Synthesis of the compound of Example 7 was completed by using procedures similar to those of Example 1. MS(ESI) m/z(M+1)+: 517.11.

Example 8: N-(4-((6,7-dimethoxyquinolin-4-yl)oxy)phenyl)-2-(3-(trifluoromethyl)phenyl)acetamide

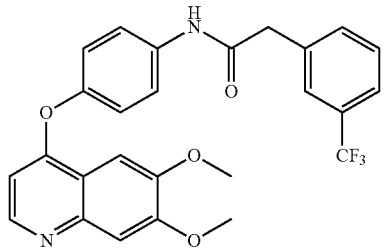 [SMILES: COc1cc2nccc(Oc3ccc(NC(=O)Cc4cccc(C(F)(F)F)c4)cc3)c2cc1OC]

Synthesis of the compound of Example 8 was completed by using procedures similar to those of Example 1. MS(ESI) m/z(M+1)+: 483.15.

Example 9: N-(4-((6,7-dimethoxyquinolin-4-yl)oxy)phenyl)-2-(4-(trifluoromethyl)phenyl)acetamide

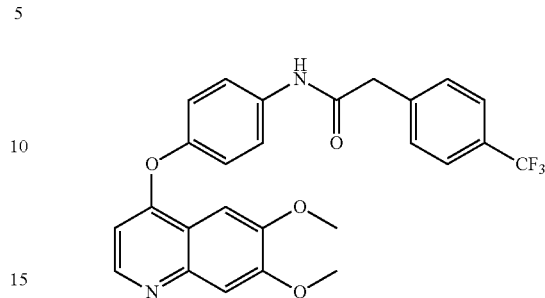

Synthesis of the compound of Example 9 was completed by using procedures similar to those of Example 1. MS(ESI) m/z(M+1)+: 483.15.

Example 10: N-(4-((6,7-dimethoxyquinolin-4-yl)oxy)phenyl)-2-(3,4-dimethoxyphenyl)acetamide

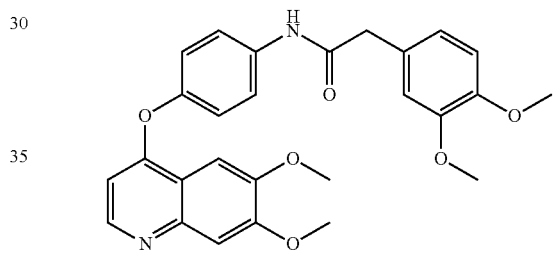

Synthesis of the compound of Example 10 was completed by using procedures similar to those of Example 1. MS(ESI) m/z(M+1)+: 475.18.

Example 11: N-(4-((6,7-dimethoxyquinolin-4-yl)oxy)phenyl)-2-(3,4-dimethylphenyl)acetamide

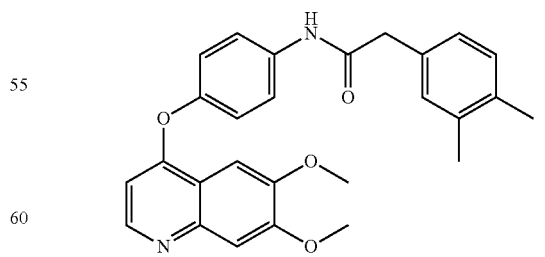

Synthesis of the compound of Example 11 was completed by using procedures similar to those of Example 1. MS(ESI) m/z(M+1)+: 443.19.

Example 12: N-(4-((6,7-dimethoxyquinolin-4-yl)oxy)phenyl)-2-(3,4-difluorophenyl)acetamide

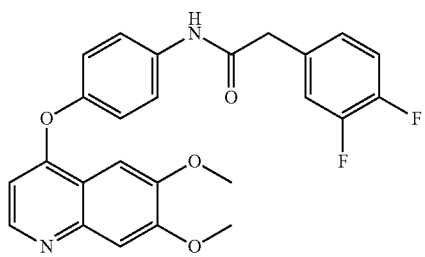 [SMILES: COc1cc2nccc(Oc3ccc(NC(=O)Cc4ccc(F)c(F)c4)cc3)c2cc1OC]

Synthesis of the compound of Example 12 was completed by using procedures similar to those of Example 1. MS(ESI) m/z(M+1)+: 451.14.

Example 13: N-(4-((6,7-dimethoxyquinolin-4-yl)oxy)phenyl)-2-(4-fluoro-3-(trifluoromethyl)phenyl)acetamide

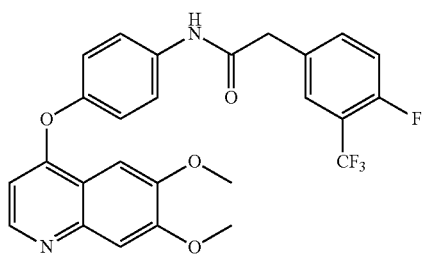

Synthesis of the compound of Example 13 was completed by using procedures similar to those of Example 1. MS(ESI) m/z(M+1)+: 501.14.

Example 14: N-(4-((6,7-dimethoxyquinolin-4-yl)oxy)phenyl)-2-(2,6-difluorophenyl)acetamide

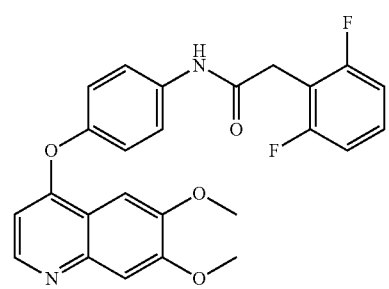 [SMILES: COc1cc2nccc(Oc3ccc(NC(=O)Cc4c(F)cccc4F)cc3)c2cc1OC]

Synthesis of the compound of Example 14 was completed by using procedures similar to those of Example 1. MS(ESI) m/z(M+1)+: 451.14.

Example 15: N-(4-((6,7-dimethoxyquinolin-4-yl)oxy)phenyl)-2-(2,4-difluorophenyl)acetamide

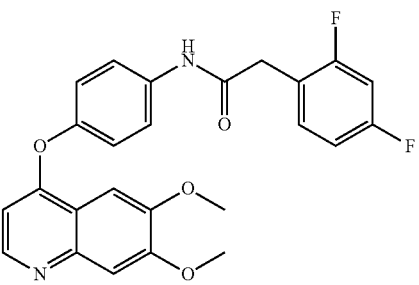 [SMILES: COc1cc2nccc(Oc3ccc(NC(=O)Cc4ccc(F)cc4F)cc3)c2cc1OC]

Synthesis of the compound of Example 15 was completed by using procedures similar to those of Example 1. MS(ESI) m/z(M+1)+: 451.14.

Example 16: N-(4-((6,7-dimethoxyquinolin-4-yl)oxy)phenyl)-2-(3-fluoro-4-methylphenyl)acetamide

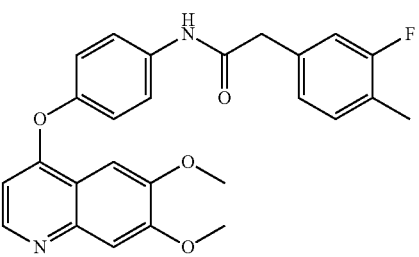 [SMILES: COc1cc2nccc(Oc3ccc(NC(=O)Cc4ccc(C)c(F)c4)cc3)c2cc1OC]

Synthesis of the compound of Example 16 was completed by using procedures similar to those of Example 1. MS(ESI) m/z(M+1)+: 447.17.

Example 17: N-(4-((6,7-dimethoxyquinolin-4-yl)oxy)phenyl)-2-(3,4-dichlorophenyl)acetamide

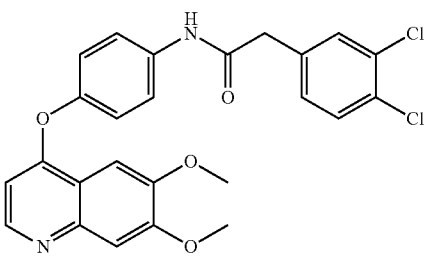 [SMILES: COc1cc2nccc(Oc3ccc(NC(=O)Cc4ccc(Cl)c(Cl)c4)cc3)c2cc1OC]

Synthesis of the compound of Example 17 was completed by using procedures similar to those of Example 1. MS(ESI) m/z(M+1)+: 483.08.

Example 18: N-(4-((6,7-dimethoxyquinolin-4-yl)oxy)phenyl)-2-(benzo[d][1,3]dioxol-5-yl)acetamide

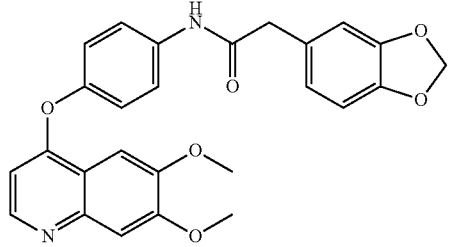 [SMILES: COc1cc2nccc(Oc3ccc(NC(=O)Cc4ccc5c(c4)OCO5)cc3)c2cc1OC]

Synthesis of the compound of Example 18 was completed by using procedures similar to those of Example 1. MS(ESI) m/z(M+1)+: 459.15.

Example 19: N-(4-((6,7-dimethoxyquinolin-4-yl)oxy)phenyl)-2-(naphth-2-yl)acetamide

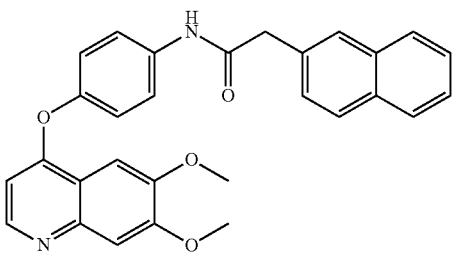 [SMILES: COc1cc2nccc(Oc3ccc(NC(=O)Cc4ccc5ccccc5c4)cc3)c2cc1OC]

Synthesis of the compound of Example 19 was completed by using procedures similar to those of Example 1. MS(ESI) m/z(M+1)+: 465.18.

Example 20: N-(4-((6,7-dimethoxyquinolin-4-yl)oxy)phenyl)-2-(3-fluorophenyl)acetamide

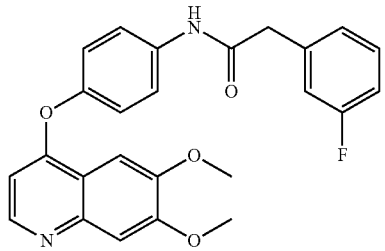 [SMILES: COc1cc2nccc(Oc3ccc(NC(=O)Cc4cccc(F)c4)cc3)c2cc1OC]

Synthesis of the compound of Example 20 was completed by using procedures similar to those of Example 1. MS(ESI) m/z(M+1)+: 433.15.

Example 21: N-(4-((6,7-dimethoxyquinolin-4-yl)oxy)phenyl)-2-(4-methylpiperazin-1-yl)acetamide

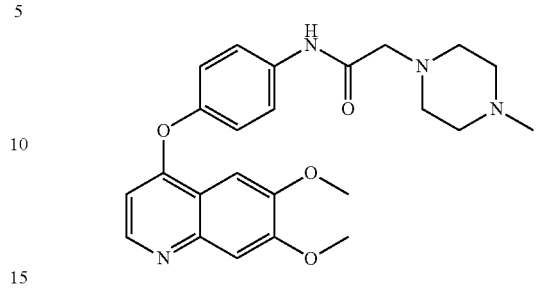

Synthesis of the compound of Example 21 was completed by using procedures similar to those of Example 1. MS(ESI) m/z(M+1)+: 437.21.

Example 22: N-(4-((6,7-dimethoxyquinolin-4-yl)oxy)phenyl)-3-(4-methylpiperazin-1-yl)propanamide

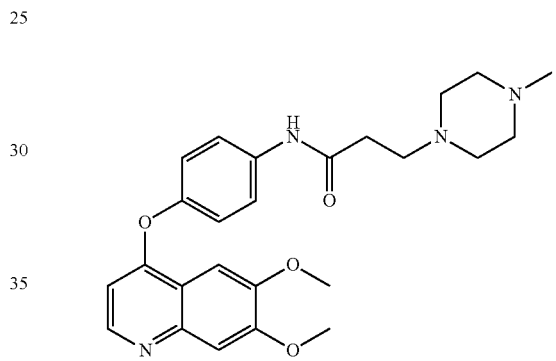

Synthesis of the compound of Example 22 was completed by using procedures similar to those of Example 1. MS(ESI) m/z(M+1)+: 451.23.

Example 23: N-(2-chloro-4-((6,7-dimethoxyquinolin-4-yl)oxy)phenyl)-2-(4-chloro-3-(trifluoromethyl)phenyl)acetamide

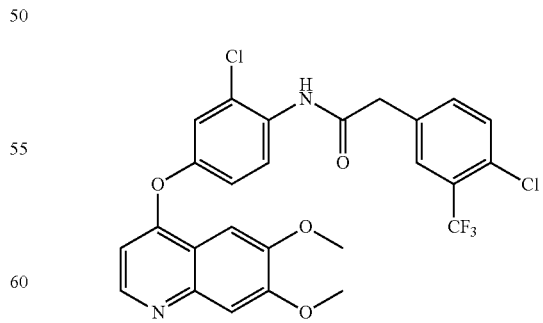

Synthesis of the compound of Example 23 was completed by using procedures similar to those of Example 1. MS(ESI) m/z(M+1)+: 551.07.

Example 24: N-(2-fluoro-4-((6,7-dimethoxyquinolin-4-yl)oxy)phenyl)-2-(4-chloro-3-(trifluoromethyl)phenyl)acetamide

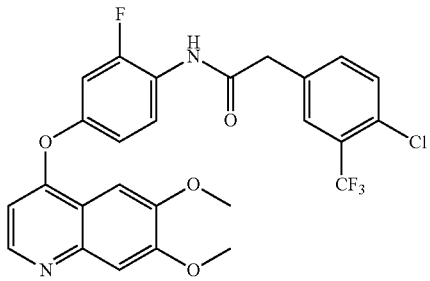 [SMILES: COc1cc2nccc(Oc3ccc(NC(=O)Cc4ccc(Cl)c(C(F)(F)F)c4)c(Cl)c3)c2cc1OC]

Synthesis of the compound of Example 24 was completed by using procedures similar to those of Example 1. MS(ESI) m/z(M+1)+: 535.10.

Example 25: N-(3-fluoro-4-((6,7-dimethoxyquinolin-4-yl)oxy)phenyl)-2-(4-chloro-3-(trifluoromethyl)phenyl)acetamide

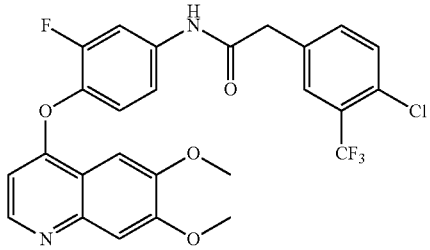

Synthesis of the compound of Example 25 was completed by using procedures similar to those of Example 1. MS(ESI) m/z(M+1)+: 535.10.

Example 26: N-(2-methyl-4-((6,7-dimethoxyquinolin-4-yl)oxy)phenyl)-2-(4-chloro-3-(trifluoromethyl)phenyl)acetamide

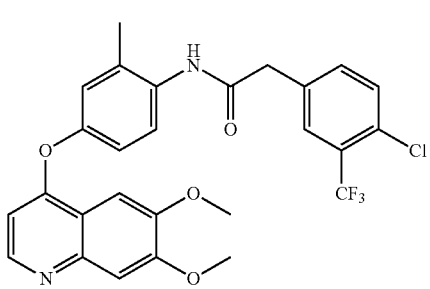 [SMILES: COc1cc2nccc(Oc3ccc(NC(=O)Cc4ccc(Cl)c(C(F)(F)F)c4)c(C)c3)c2cc1OC]

Synthesis of the compound of Example 26 was completed by using procedures similar to those of Example 1. MS(ESI) m/z(M+1)+: 531.12.

Example 27: N-(3-methyl-4-((6,7-dimethoxyquinolin-4-yl)oxy)phenyl)-2-(4-chloro-3-(trifluoromethyl)phenyl)acetamide

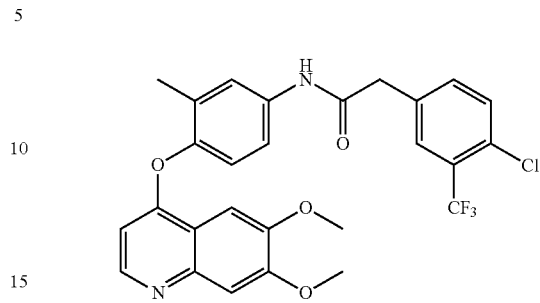

Synthesis of the compound of Example 27 was completed by using procedures similar to those of Example 1. MS(ESI) m/z(M+1)+: 531.12.

Example 28: 1-(4-((6,7-dimethoxyquinolin-4-yl)oxy)phenyl)-3-(3-morpholinopropyl)urea

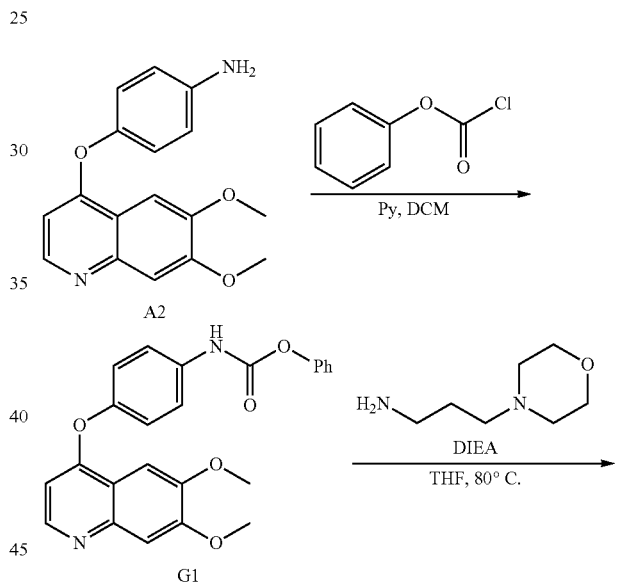

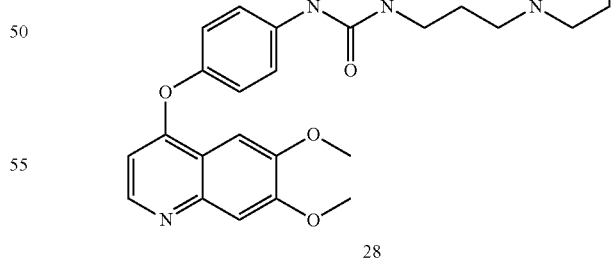

Phenyl (4-((6,7-dimethoxyquinolin-4-yl)oxy)phenyl)carbamate (G1): 4-((6,7-dimethoxyquinolin-4-yl)oxy)phenylamine (1 g) was dissolved in dichloromethane (30 ml), followed by addition of pyridine (0.4 g), and by dropwise addition of phenyl chloroformate (0.8 g) in an ice bath. Stirring was continued for 3 h. After completion of the reaction, the reaction system was added with water and extracted with dichloromethane. The organic phase was dried over anhydrous sodium sulfate and subjected to filtering. Dichloromethane was removed under reduced pressure and the residue was purified via pressurized silica gel column chromatography to obtain the Compound G1. MS: (M+1) 417.14.

1-(4-((6,7-dimethoxyquinolin-4-yl)oxy)phenyl)-3-(3-morpholinopropyl)urea (42): to a round-bottom flask was added phenyl (4-((6,7-dimethoxyquinolin-4-yl)oxy)phenyl) carbamate (50 mg), N-(3-aminopropyl)morpholine (26 mg), N,N-diisoproypylethylamine (23 mg) and tetrahydrofuran (3 ml). The reaction mixture was allowed to react overnight at 80° C. After completion of the reaction, the reaction system was concentrated and the residue was purified via pressurized silica gel column chromatography to obtain Compound 28. MS: (M+1) 467.22.

Example 29: 1-(4-((6,7-dimethoxyquinolin-4-yl)oxy)phenyl)-3-(3-(4-methylpiperazin-1-yl)propyl)urea

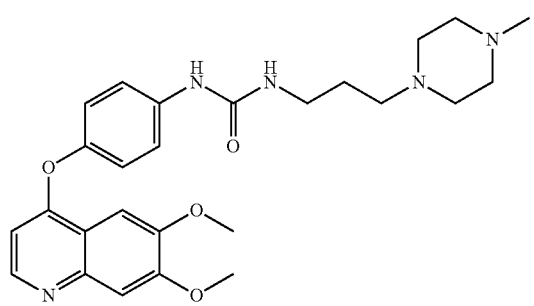 [SMILES: COc1cc2nccc(Oc3ccc(NC(=O)NCCCN4CCN(C)CC4)cc3)c2cc1OC]

Example 30: 1-(4-((6,7-dimethoxyquinolin-4-yl)oxy)phenyl)-3-(3-phenylpropyl)urea

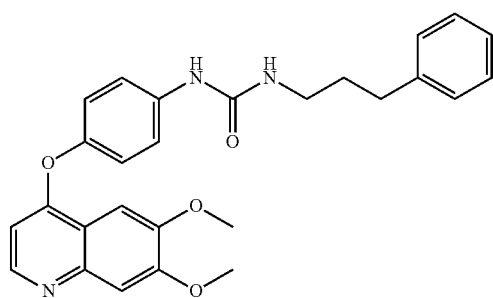 [SMILES: COc1cc2nccc(Oc3ccc(NC(=O)NCCCc4ccccc4)cc3)c2cc1OC]

Synthesis of the compound of Example 30 was completed by using procedures similar to those of Example 28. MS(ESI) m/z(M+1)+: 458.20.

Example 31: 1-(4-((6,7-dimethoxyquinolin-4-yl)oxy)phenyl)-3-(3-(3-fluorophenyl)propyl)urea

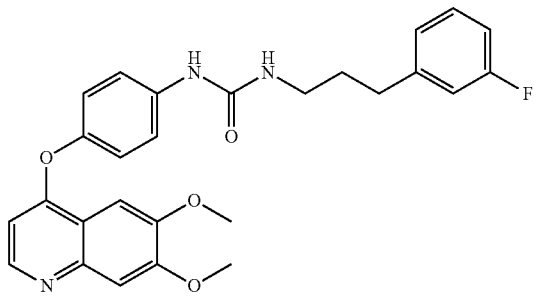 [SMILES: COc1cc2nccc(Oc3ccc(NC(=O)NCCCc4cccc(F)c4)cc3)c2cc1OC]

Synthesis of the compound of Example 31 was completed by using procedures similar to those of Example 28. MS(ESI) m/z(M+1)+: 476.19.

Example 32: 1-(4-((6,7-dimethoxyquinolin-4-yl)oxy)phenyl)-3-(3-(4-fluorophenyl)propyl)urea

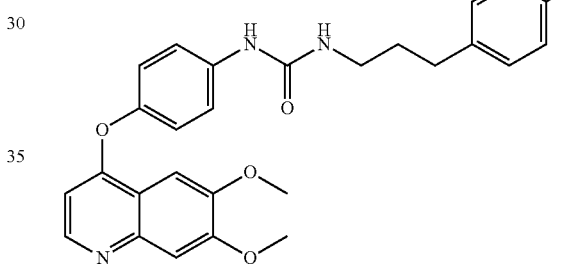

Synthesis of the compound of Example 32 was completed by using procedures similar to those of Example 28. MS(ESI) m/z(M+1)+: 476.19.

Example 33: 1-(4-((6,7-dimethoxyquinolin-4-yl)oxy)phenyl)-3-(3-(3-(trifluoromethyl)phenyl)propyl)urea

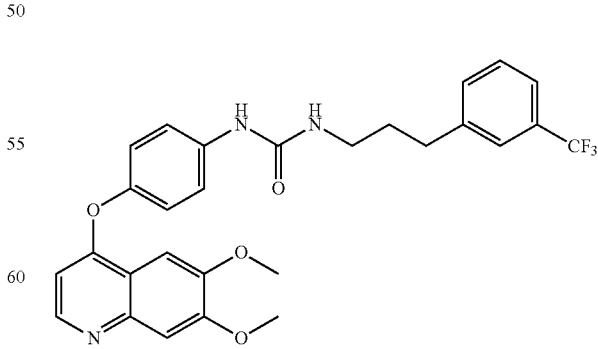

Synthesis of the compound of Example 33 was completed by using procedures similar to those of Example 28. MS(ESI) m/z(M+1)+: 526.19.

Example 34: (1-(4-((6,7-dimethoxyquinolin-4-yl)oxy)phenyl)-3-(3-(3-(methyl)phenyl)propyl)urea

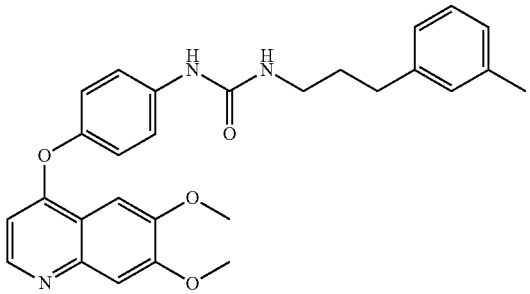 [SMILES: COc1cc2nccc(Oc3ccc(NC(=O)NCCCc4cccc(C)c4)cc3)c2cc1OC]

Synthesis of the compound of Example 34 was completed by using procedures similar to those of Example 28. MS(ESI) m/z(M+1)+: 472.22.

Example 35: 1-(4-((6,7-dimethoxyquinolin-4-yl)oxy)phenyl)-3-(3-(4-(trifluoromethyl)phenyl)propyl)urea

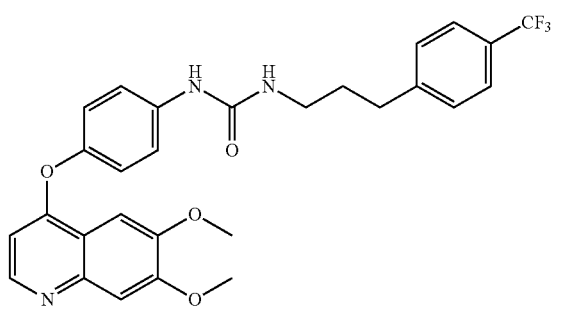 [SMILES: COc1cc2nccc(Oc3ccc(NC(=O)NCCCc4ccc(C(F)(F)F)cc4)cc3)c2cc1OC]

Synthesis of the compound of Example 35 was completed by using procedures similar to those of Example 28. MS(ESI) m/z(M+1)+: 526.19.

Example 36: N-(3-trifluoromethyl-4-((6,7-dimethoxyquinolin-4-yl)oxy)phenyl)-2-(4-chloro-3-(trifluoromethyl)phenyl)acetamide

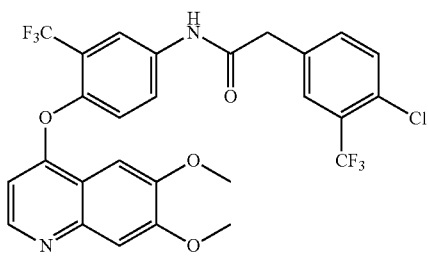

Synthesis of the compound of Example 36 was completed by using procedures similar to those of Example 1. MS(ESI) m/z(M+1)+: 585.10.

Example 37: N-(3-methoxy-4-((6,7-dimethoxyquinolin-4-yl)oxy)phenyl)-2-(4-chloro-3-(trifluoromethyl)phenyl)acetamide

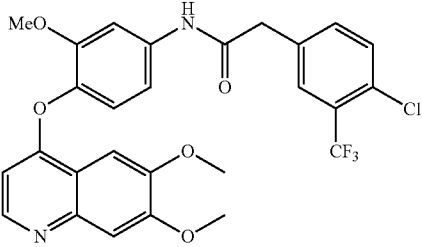

Synthesis of the compound of Example 37 was completed by using procedures similar to those of Example 1. MS(ESI) m/z(M+1)+: 547.12.

Example 38: N-(3-chloro-4-((6,7-dimethoxyquinolin-4-yl)oxy)phenyl)-2-(4-chloro-3-(trifluoromethyl)phenyl)acetamide

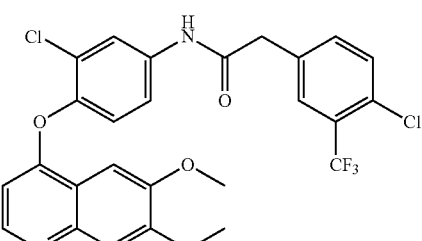

Synthesis of the compound of Example 38 was completed by using procedures similar to those of Example 1. MS(ESI) m/z(M+1)+: 551.08.

Example 39: N-(3-cyano-4-((6,7-dimethoxyquinolin-4-yl)oxy)phenyl)-2-(4-chloro-3-(trifluoromethyl)phenyl)acetamide

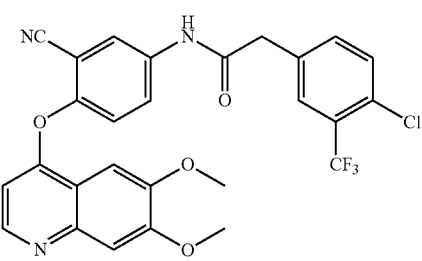 [SMILES: COc1cc2nccc(Oc3ccc(NC(=O)Cc4ccc(Cl)c(C(F)(F)F)c4)cc3C#N)c2cc1OC]

Synthesis of the compound of Example 39 was completed by using procedures similar to those of Example 1. MS(ESI) m/z(M+1)+: 542.11.

Example 40: N-(4-((6,7-dimethoxyquinolin-4-yl)oxy)phenyl)-2-(2-(trifluoromethyl)phenyl)acetamide

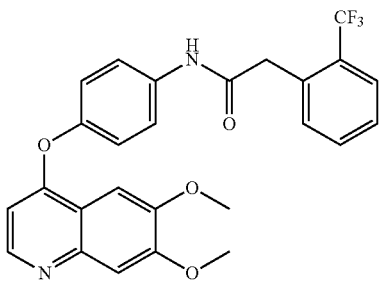 [SMILES: COc1cc2nccc(Oc3ccc(NC(=O)Cc4ccccc4C(F)(F)F)cc3)c2cc1OC]

Synthesis of the compound of Example 40 was completed by using procedures similar to those of Example 1. MS(ESI) m/z(M+1)+: 483.15.

Comparative Example 1: N-(6-((6,7-dimethoxyquinolin-4-yl)oxy)pyridin-3-yl)-2-phenylacetamide

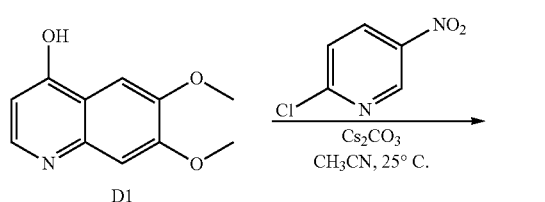

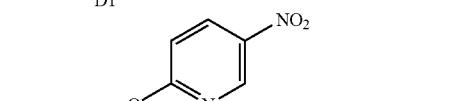

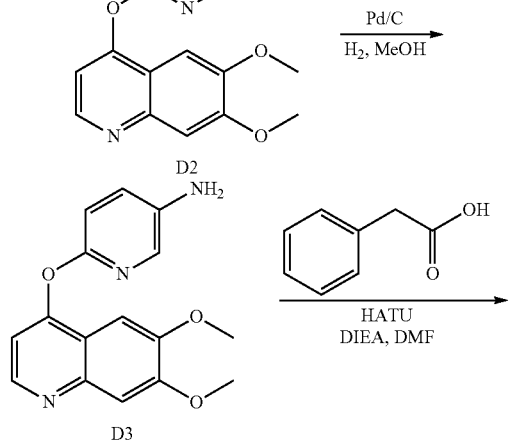

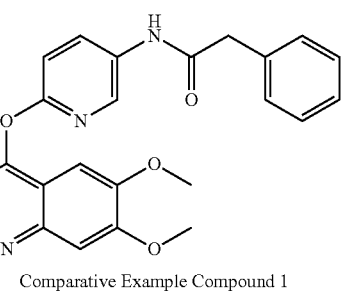

Comparative Example Compound 1

6,7-dimethoxy-4-((5-nitropyridin-2-yl)oxy)quinoline (D2): to a round-bottom flask was added 4-hydroxy-6,7-dimethoxyquinoline (0.5 g), followed by addition of acetonitrile (10 ml), and then by cesium carbonate (0.87 g). The mixture was stirred under room temperature for 5 minutes. Then 2-chloro-5-nitropyridine (0.42 g) was added and stirring was conducted overnight at room temperature. Filtering was conducted after completion of the reaction, the filtrate was concentrated and the residue was purified via pressurized silica gel column chromatography to obtain Compound D2.

6-((6,7-dimethoxyquinolin-4-yl)oxy)pyridin-3-amine (D3): to a round-bottom flask was added 6,7-dimethoxy-4-((5-nitropyridin-2-yl)oxy)quinoline (0.42 g), and followed by addition of methanol (10 ml), palladium/carbon (0.11 g). Reaction was allowed to occur overnight under hydrogen atmosphere. Filtering was conducted after completion of the reaction, the filtrate was concentrated and the residue was purified via pressurized silica gel column chromatography to obtain Compound D3. LC/MS: M+H 298.11.

N-(6-((6,7-dimethoxyquinolin-4-yl)oxy)pyridin-3-yl)-2-phenylacetamide (Comparative Example Compound 1): to a round-bottom flask was added 6-((6,7-dimethoxyquinolin-4-yl)oxy)pyridin-3-amine (50 mg), followed by addition of N,N-dimethylformamide (2 ml), HATU (96 mg), phenylacetic acid (34 mg) and N,N-diisopropylethylamine (66 mg). The reaction system was stirred overnight at room temperature. After completion of the reaction, the system was added with water and extracted with ethyl acetate, with the organic phase subjected to drying over anhydrous sodium sulfate. The organic phase was filtered, the solvent was removed from the filtrate under reduced pressure, and the residue was purified via pressurized silica gel column chromatography to obtain Comparative Example Compound 1. LC/MS: M+H 416.16.

Comparative Example 2: N-(5-chloro-6-((6,7-dimethoxyquinolin-4-yl)oxy)pyridin-3-yl)-2-(3-(trifluoromethyl)phenyl)acetamide

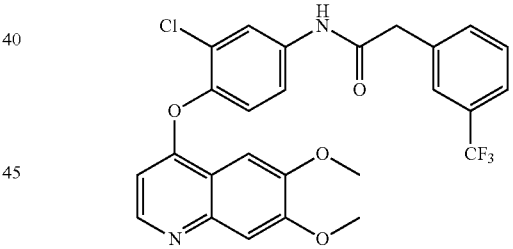

Synthesis of the compound of Comparative Example 2 was completed by using procedures similar to those of Comparative Example 1. MS(ESI) m/z(M+1)+: 518.10.

Comparative Example 3: N-(3-(trifluoromethyl)benzyl)-4-((6,7-dimethoxyquinolin-4-yl)oxy)benzamide

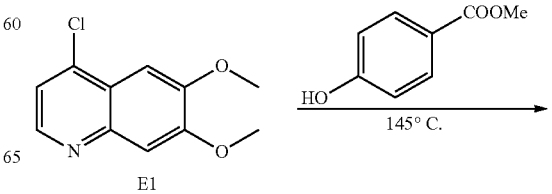

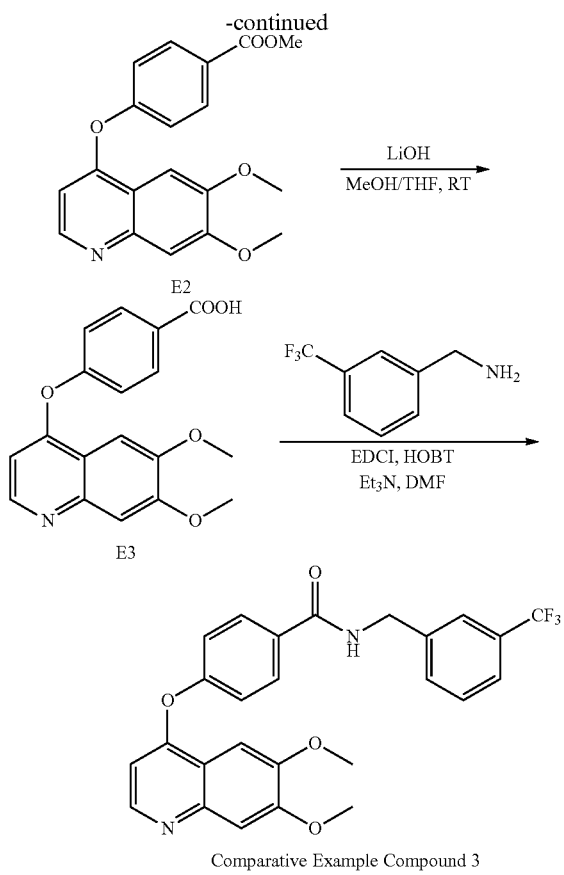

Comparative Example Compound 3

Methyl 4-((6,7-dimethoxyquinolin-4-yl)oxy)benzoate (E2): to a round-bottom flask was added 4-chloro-6,7-dimethoxyquinoline (1.0 g) and methyl 4-hydroxybenzoate (0.68 g), and the mixture was stirred overnight at 145° C. After completion of the reaction, the mixture was added with saturated sodium bicarbonate solution, extracted with ethyl acetate, and the organic phase was dried over anhydrous sodium sulfate and filtered. The filtrate was concentrated and the residue was purified via pressurized silica gel column chromatography to obtain Compound E2.

4-((6,7-dimethoxyquinolin-4-yl)oxy)benzoic acid (E3): to a round-bottom flask was added methyl 4-((6,7-dimethoxyquinolin-4-yl)oxy)benzoate (0.5 g), methanol/tetrahydrofuran (5:1, 10 ml), and lithium hydroxide (0.18 g). Reaction was allowed to occur overnight at room temperature. Concentration was conducted after completion of the reaction, and pH was adjusted to about 5 with concentrated hydrochloric acid. Filtering was conducted and the filter cake was washed with water to obtain the Compound E3. LC/MS: M+H 326.10.

N-(3-(trifluoromethyl)benzyl)-4-((6,7-dimethoxyquinolin-4-yl)oxy)benzamide (Comparative Example Compound 3): to a round-bottom flask was added 4-((6,7-dimethoxyquinolin-4-yl)oxy)benzoic acid (20 mg), and followed by addition of N,N-dimethylformamide (2 ml), 3-trifluoromethylbenzylamine (13 mg), EDCI (17 mg), HOBT (12 mg) and triethylamine (12 mg). The reaction system was stirred overnight at room temperature. After completion of the reaction, the system was added with water and extracted with ethyl acetate, with the organic phase subjected to drying over anhydrous sodium sulfate. The organic phase was filtered and the solvent was removed from the filtrate under reduced pressure. The residue was purified via pressurized silica gel column chromatography to obtain Comparative Example Compound 3. LC/MS: M+H 483.15.

Comparative Example 4: N-(4-((6,7-dimethoxyquinazolin-4-yl)oxy)phenyl)-2-(3-methoxyphenyl)acetamide

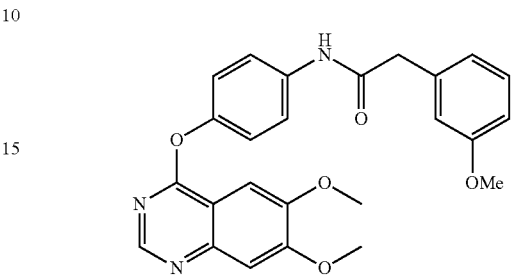

Synthesis of the compound of Comparative Example 4 was completed by using procedures similar to those of Example 1. MS(ESI) m/z(M+1)+: 446.17.

Example 41: Effects on Proliferation of Cancer Cells

Compounds as provided herein were further evaluated for their inhibitory effects on proliferation of cancer cells by testing their effects on growth of cancer cells. In this example the following cells were used: primary mouse B cells BaF3 (purchased from ATCC), GIST-T1 cells of the human gastrointestinal stromal tumor cell line (expressing wild-type KIT gene) (purchased from Cosmo Bio Co., Ltd. (Japan)). The present lab further constructed and used the following: mouse Tel-Kit-BaF3 (stably expressing KIT wild-type kinase), mouse Tel-Kit/T670I-BaF3 (stably expressing KIT T670I mutant kinase), mouse Tel-Kit/V559A-BaF3 (stably expressing KIT V559A mutant kinase), mouse Tel-Kit/V559D-BaF3 (stably expressing KIT V559D mutant kinase), mouse Tel-Kit/V559G-BaF3 (stably expressing KIT V559G mutant kinase), mouse Tel-Kit/V560D-BaF3 (stably expressing KIT V560D mutant kinase), mouse Tel-Kit/L576P-BaF3 (stably expressing KIT L576P mutant kinase), mouse Tel-Kit/V654A-BaF3 (stably expressing KIT V654A mutant kinase), mouse Tel-Kit/V654A/V559D-BaF3 (stably expressing KIT V654A V559D mutant kinase), mouse Tel-Kit/T670E-BaF3 (stably expressing KIT T670E mutant kinase), mouse Tel-Kit/T670I/V559D-BaF3 (stably expressing KIT T670I V559D mutant kinase), mouse Tel-Kit/S709F-BaF3 (stably expressing KIT S709F mutant kinase), mouse Tel-Kit/D816E-BaF3 (stably expressing KIT D816E mutant kinase), mouse Tel-Kit/D816H-BaF3 (stably expressing KIT D816H mutant kinase), mouse Tel-Kit/D820E-BaF3 (stably expressing KIT D820E mutant kinase), mouse Tel-Kit/D820G-BaF3 (stably expressing KIT D820G mutant kinase), mouse Tel-Kit/D820Y-BaF3 (stably expressing KIT D820Y mutant kinase), mouse Tel-Kit/N822K-BaF3 (stably expressing KIT N822K mutant kinase), mouse Tel-Kit/Y823D-BaF3 (stably expressing KIT Y823D mutant kinase), mouse Tel-Kit/A829P-BaF3 (stably expressing KIT A829P mutant kinase), GIST-T1-T670I cells of the human gastrointestinal stromal tumor cell line (expressing KIT-T670I mutant gene). The above cell lines were constructed by: amplifying respectively the sequences of human KIT and various mutant kinase regions of KIT via PCR, inserting the fragments respectively into MSCV-Puro vectors having a N-terminal TEL fragment and/or a NPM fragment and/or a TPR fragment (purchased from Clontech), transfecting mouse BaF3 cells with the vectors by means of retrovirus to obtain stably transfected cells, removing the growth factor IL-3, and thereby eventually obtaining cell lines that depend on the transferred protein KIT or various mutants of KIT. The GIST-T1-T670I (expressing C-KIT-T670I mutant gene) cell line was constructed by our laboratory as follows: designing sgRNA that targeted a region around T670 of the KIT gene with CRISPR Design Tool (website: crispr.mit.edu, Zhang Feng Lab), cloning it into pSpCas9(BB)-2A-Puro vector; co-transfecting cells with the resultant vector and a single-stranded oligonucleotide having T670I site mutation that is near to T670, subjecting the resultant to antibiotics screening, followed by dilution, and monocellular culture in a 96-well plate; validating the site T670 of the cells by sequence detection via Sanger sequencing.

In the example the above cells were added with the compounds of the present invention at different concentrations (0.000508 µM, 0.00152 µM, 0.00457 µM, 0.0137 µM, 0.0411 µM, 0.123 µM, 0.370 µM, 1.11 µM, 3.33 µM, 10 µM), imatinib (Imatinib, MedChem Express, China) and sunitinib (Sunitinib, MedChem Express, China) as prior art compounds, as well as Comparative Example Compounds 1-4, and incubated for 72 hours. The cells after incubation were detected using CCK-8 (purchased from MedChem Express, Shanghai, China) cell viability assay kit (CCK-8 may be reduced by dehydrogenase in living cells to a highly water-soluble yellow formazan product, and the amount of the resultant formazan is proportional to the number of living cells), the number of living cells were quantified with a microplate reader, and $GI_{50}$ of the compounds and the control compounds were calculated (the results shown in Table 2 and Table 3).

The experimental results in Table 2 showed that, the compounds of the present invention exhibited certain inhibitory effects against both wild-type KIT and mutant KIT-T670I. As to Comparative Example Compounds 1 and 2, the structures of which were similar to the compounds of the preset invention but differed in that the phenyl ring in the middle of the compound backbone was substituted with a pyridine ring, it was found after testing that the Comparative Example Compounds 1 and 2 exhibited no significant inhibitory effects against wild-type KIT and mutant KIT-T670I. When the positions of the amino and the carbonyl in the backbone of the compound are changed, e.g., Comparative Example Compound 3, the activity against KIT and KIT-T670I substantially vanished. Comparative Example Compound 4, which contained a quinazoline backbone instead of the quinoline backbone of the present invention compounds, exhibited certain inhibitory activity but lower than that of the present invention compounds against cKIT and cKIT-T670I, and also a weaker selectivity against BaF3. In contrast, the present invention compounds exhibited significant selective inhibition against wild-type KIT and mutant KIT-T670I relative to parent BaF3 cells, indicating that the present invention compounds had strong inhibitory effects to the target cKIT and the T670I mutant.

Table 3 showed that Compound 1 and Compound 2 exhibited a strong inhibitory effect on KIT mutant cells which exhibited imitinib resistance and/or sunitinib resistance, indicating that the compounds of the present invention were useful in treating KIT mutation-caused diseases that are resistant to imitinib and/or sunitinib. According to the tests on the GIST-T1 (a gastrointestinal stromal tumor cell line) and on the GIST-T1-T670I cell lines (constructed by our laboratory, having mutation that caused resistance to imaitinib), it was found that, the compounds of the present invention not only inhibited strong inhibitory effects against gastrointestinal stromal tumor cells that were sensitive to imatinib, but also strong inhibitory effects against GIST-T1-T670I which were resistant to imatinib. It demonstrated that the compounds of the present invention may be useful in treating gastrointestinal stromal tumor having KIT mutations.

TABLE 2

| $GI_{50}$/µM | BaF3 | TEL-KIT-BaF3 | TEL-KIT/T670I-BaF3 |
|---|---|---|---|
| Example 1 | 7.26 | 0.017 | 0.014 |
| Example 2 | 5.97 | 0.001 | 0.004 |
| Example 8 | 1.89 | 0.02 | 0.001 |
| Example 9 | 2.16 | 0.022 | 0.011 |
| Example 11 | 6.42 | 0.027 | 0.015 |
| Example 13 | 1.03 | 0.024 | 0.013 |
| Example 24 | 3.21 | 0.049 | 0.018 |
| Example 30 | 2.91 | 0.11 | 0.01 |
| Example 31 | 2.48 | 0.097 | 0.016 |
| Example 32 | 3.85 | 0.068 | 0.015 |
| Example 38 | 9.45 | 0.078 | 0.056 |
| Comparative Example 1 | >10 | >10 | >10 |
| Comparative Example 2 | 7.1 | >10 | 9.93 |
| Comparative Example 3 | 10 | 2.35 | 4.61 |
| Comparative Example 4 | 3.12 | 0.183 | 0.844 |

TABLE 3

| $GI_{50}$/µM | Imatinib | Sunitinib | Compound 1 | Compound 2 |
|---|---|---|---|---|
| TEL-KIT/V559A-BaF3 | 0.905 | 0.02 | 0.016 | 0.021 |
| TEL-KIT/V559D-BaF3 | 0.01 | 0.001 | 0.004 | 0.006 |
| TEL-KIT/V559G-BaF3 | 0.008 | 0.004 | <0.0003 | <0.0003 |
| TEL-KIT/V560D-BaF3 | 0.003 | 0.035 | 0.005 | 0.004 |
| TEL-KIT/L576P-BaF3 | 0.085 | 0.006 | 0.002 | 0.001 |
| TEL-KIT/V654A/V559D-BaF3 | 0.608 | 0.019 | 0.039 | 0.042 |
| TEL-KIT/V654A-BaF3 | 1.41 | 0.005 | 0.11 | 0.32 |
| TEL-KIT/T670E-BaF3 | 4.08 | 0.089 | 0.053 | 0.071 |
| TEL-KIT/T670I-BaF3 | >10 | 0.021 | 0.014 | 0.004 |
| TEL-KIT/T670I/V559D-BaF3 | >10 | 0.012 | 0.048 | 0.045 |
| TEL-KIT/S709F-BaF3 | 0.115 | 0.028 | 0.011 | 0.017 |
| TEL-KIT/D816E-BaF3 | 0.174 | 0.059 | 0.009 | 0.016 |
| TEL-KIT/D816H-BaF3 | 0.651 | 0.315 | 0.058 | 0.097 |
| TEL-KIT/D820E-BaF3 | 0.035 | 0.093 | 0.005 | 0.001 |
| TEL-KIT/D820G-BaF3 | 0.337 | 0.389 | 0.009 | 0.009 |
| TEL-KIT/D820Y-BaF3 | 0.435 | 0.172 | 0.006 | 0.003 |
| TEL-KIT/N822K-BaF3 | 1.47 | 0.384 | 0.069 | 0.026 |
| TEL-KIT/Y823D-BaF3 | 5.87 | 0.704 | 0.015 | 0.035 |
| TEL-KIT/A829P-BaF3 | 0.58 | 0.18 | 0.008 | 0.022 |
| GIST-T1 | 0.015 | 0.011 | 0.005 | 0.006 |
| GIST-T1/T670I | >10 | 0.004 | 0.016 | 0.011 |

Example 42: Animal Experiments

In this example Compound 1 and Compound 2 were respectively tested in TEL-cKIT/T670I-BaF3, TEL-cKIT/Y823D-BaF3, TEL-cKIT/D820G-BaF3 and GIST-T1-T670I mouse models.

Experimental protocols were as follows.

(1) Bal b/c female mice aged 4-6 weeks were purchased from Beijing Weitong Lihua Laboratory Animal Co., Ltd., and the mice were raised in an SPF laboratory.

The drinking water and padding were sterilized by autoclaving. All operations on mice were conducted under aseptic conditions.

(2) About 5×10⁶ TEL-cKIT/T670I-BaF3, TEL-cKIT/Y823D-BaF3, TEL-cKIT/D820G-BaF3 or GIST-T1-T670I cells were respectively injected subcutaneously onto the left back of all mice on Day 0.

(3) From Day 6, for the TEL-cKIT/T670I-BaF3 mouse model the corresponding mice were administrated orally every day with methylcellulose (HKI) as the vehicle (5 mice); with Compound 1 and Compound 2 at a dosage of 10 mg/kg, 20 mg/kg, 40 mg/kg, 100 mg/kg mouse weight (5 mice in each group); and with Sunitnib (purchased from MedChemExpress, China) at a dosage of 40 mg/kg mouse weight (5 mice). From day 6, for the TEL-cKIT/Y823D-BaF3 and TEL-cKIT/D820G-BaF3 mouse models the corresponding mice were administrated orally every day with methylcellulose (HKI) as the vehicle (5 mice); with Compound 1 and Compound 2 at a dosage of 40 mg/kg, 80 mg/kg mouse weight (5 mice in each group); and with Sunitnib (purchased from MedChemExpress, China) at a dosage of 40 mg/kg mouse weight (5 mice). From day 15, for the GIST-T1-T670I mouse model the corresponding mice were administrated orally every day with methylcellulose (HKI) as the vehicle (5 mice); with Compound 1 and Compound 2 at a dosage of 20 mg/kg, 40 mg/kg, 80 mg/kg mouse weight (5 mice in each group); and with Sunitnib at a dosage of 40 mg/kg mouse weight (5 mice).

(4) From day 6 (TEL-cKIT/T670I-BaF3, TEL-cKIT/Y823D-BaF3, TEL-cKIT/D820G-BaF3 mouse model) and From day 15 (GIST-T1-T670I mouse model), respectively, the length/width of the subcutaneous tumor were measured with a vernier caliper every day and the body weight of the mouse was recorded every day so as to determine the effects of Compound 1 and Compound 2 on the body weight and tumor size of the mice, respectively.

(5) The mice were sacrificed on Day 11 after administration for the TEL-cKIT/T670I-BaF3 mouse model, on Day 9 after administration for the TEL-cKIT/Y823D-BaF3 and TEL-cKIT/D820G-BaF3 mouse models, and on Day 28 after administration for the GIST-T1-T670I mouse model. The subcutaneous tumors were taken out, and the tumors were weighed and compared.

(6) The growth trend of subcutaneous tumors was calculated and the tumor size was calculated according to: length×width×width/2 mm³.

Figure 1B:
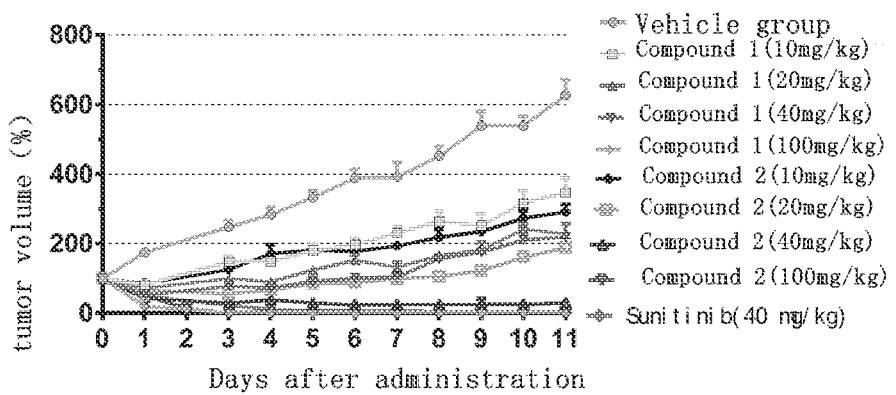
Figure 1C:
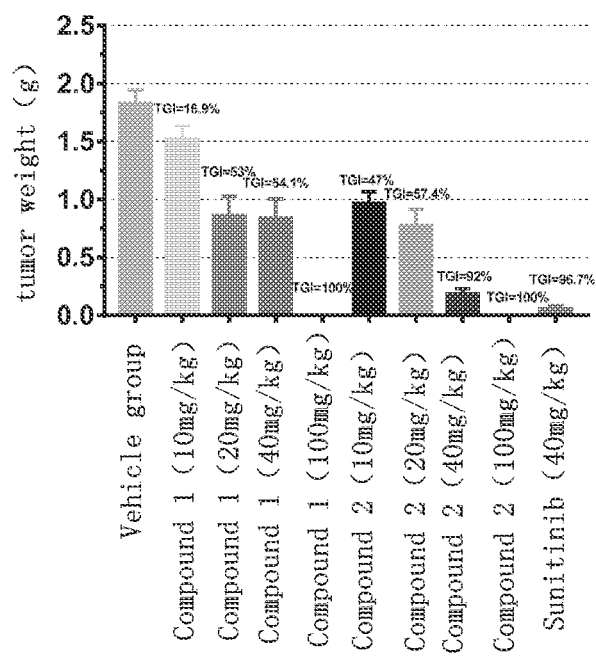
Figure 2A:
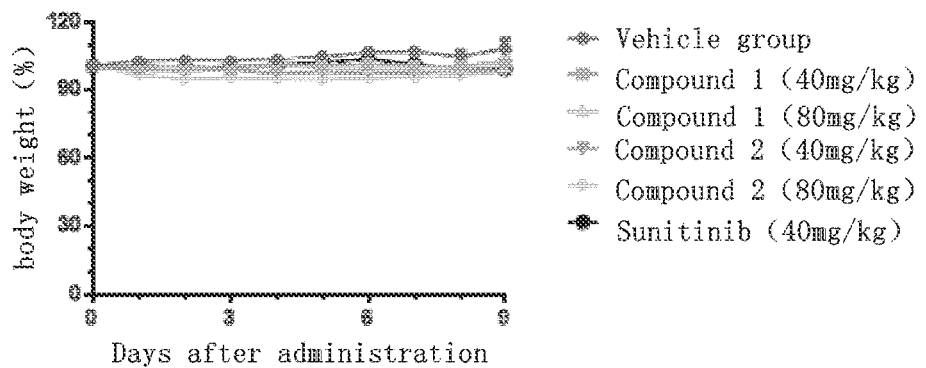
FIGS. 2a-2c show the tumor inhibitory effects of Compound 1 and Compound 2 in a tumor-grafted mouse model established with tel-cKIT/Y823D-BaF3 cells.
Figure 2B:
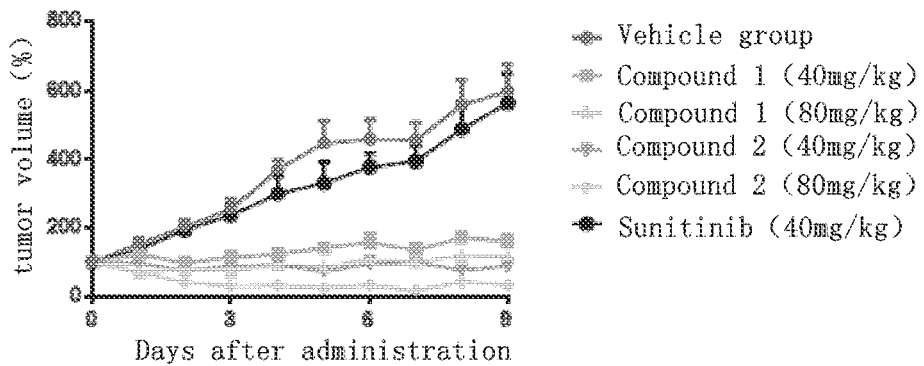
Figure 2C:
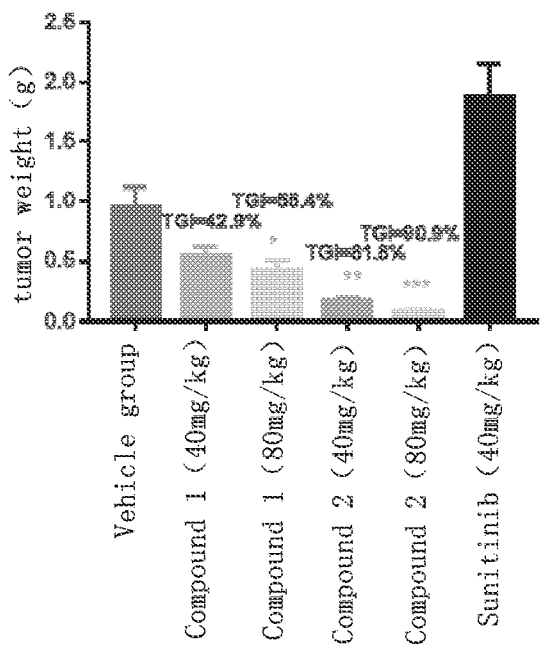
Figure 3A:
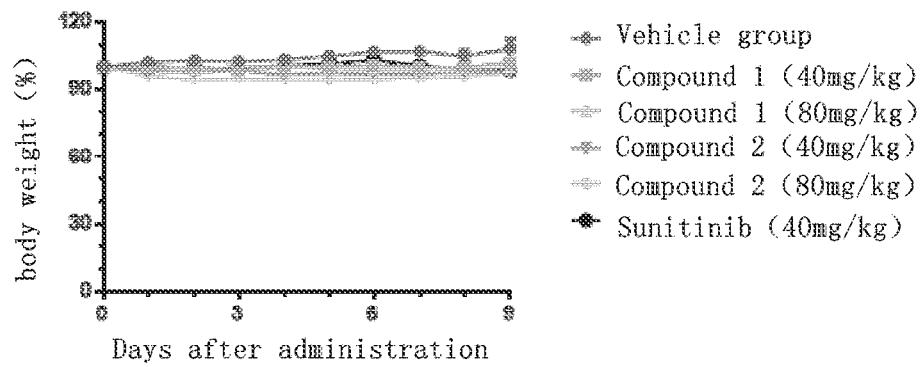
FIGS. 3a-3c show the tumor inhibitory effects of Compound 1 and Compound 2 in a tumor-grafted mouse model established with tel-cKIT/D820G-BaF3 cells.
Figure 3B:
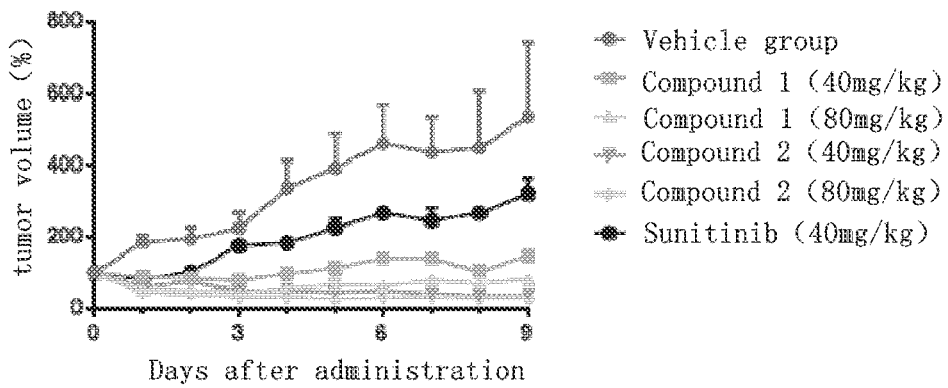
Figure 3C:
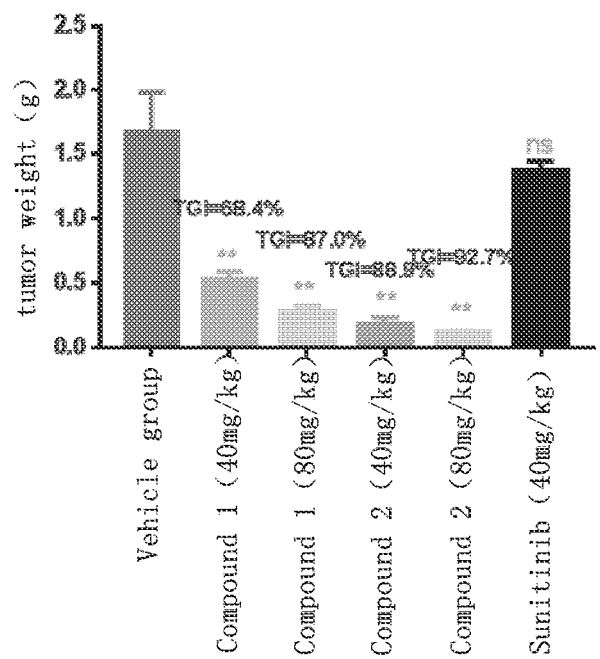
Figure 4A:
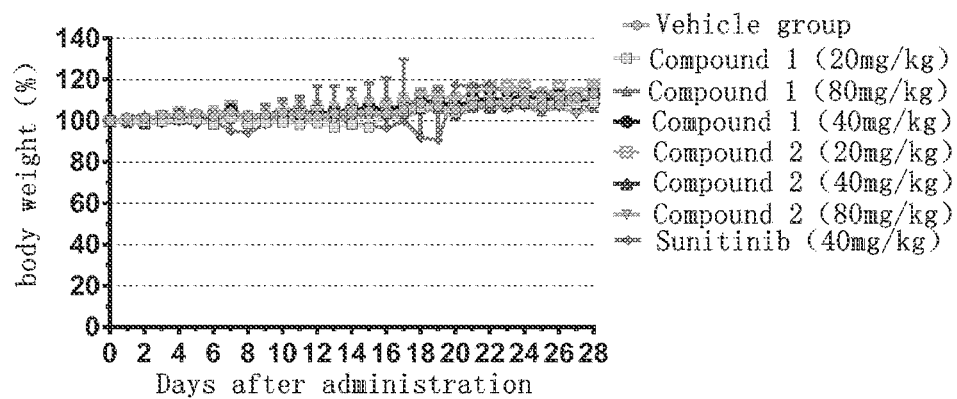
FIGS. 4a-4c show the tumor inhibitory effects of Compound 1 and Compound 2 in a tumor-grafted mouse model established with GIST-T1-T670I cells.
Figure 4B:
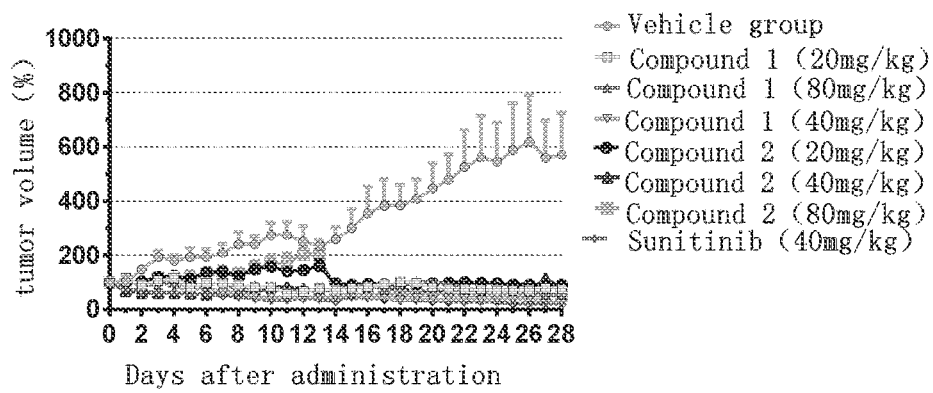
Figure 4C:
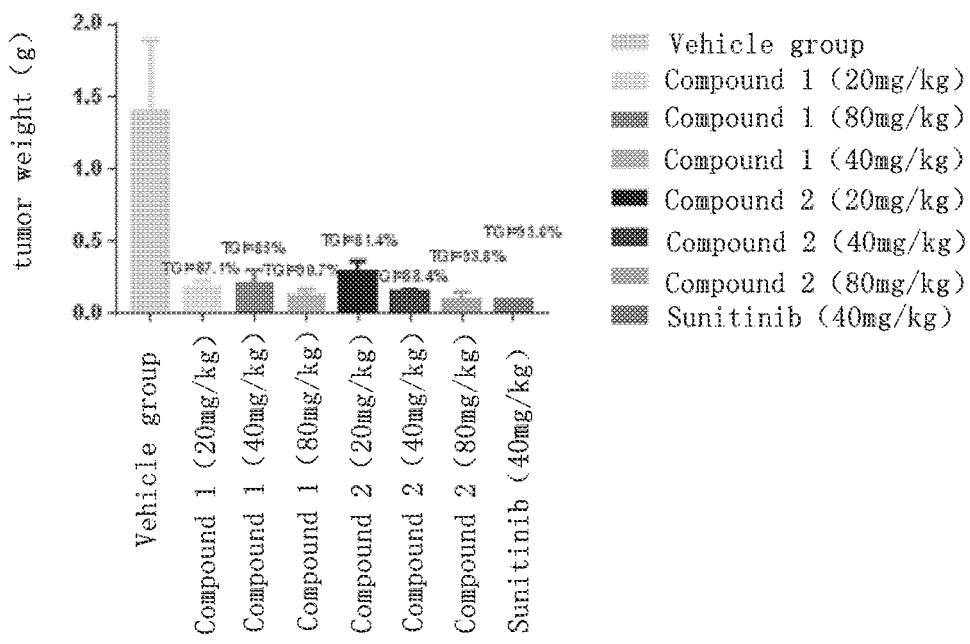

Experimental results were shown in FIGS. 1a-1c, 2a-2c, 3a-3c, and 4a-4c. In the mouse tumor models of TEL-cKIT/T670I-BaF3, TEL-cKIT/Y823D-BaF3, TEL-cKIT/D820G-BaF3 and GIST-T1-T670I, Compound 1 and Compound 2 showed excellent inhibitory effects against tumor in mice at a dosage of 40 mg/kg, and Compound 1 and Compound 2 exhibited more significant inhibitory effects against tumor in mice as the days of administration increased, especially, the tumor inhibition rate were all 80% or more when Compound 2 was administrated at 40 mg/kg. Compound 1 and Compound 2 can effectively inhibit the growth of tumor in mice without significant influence on mice weight, suggesting that Compound 1 and Compound 2 may be applicable for administration in animals. In addition, the results in the TEL-cKIT/Y823D-BaF3 and TEL-cKIT/D820G-BaF3 models also confirmed that Compound 1 and Compound 2 of the present invention have potential therapeutical effects against diseases caused by KIT mutation that is resistant to Sunitnib. Therefore, Compound 1 and Compound 2 may be used to treat gastrointestinal stromal tumor associated with KIT mutation.

INDUSTRIAL APPLICABILITY

The present invention provides a selective KIT kinase inhibitor, which may be useful in inhibiting the activity of wild-type and/or mutant KIT kinase, and also useful in treating, preventing or ameliorating diseases, disorders or conditions that are modulated or otherwise affected by kinase activity of wild-type KIT and/or mutant KIT or in which kinase activity of wild-type KIT and/or mutant KIT is implicated. Thus, the compound of the present invention may be prepared into corresponding medicaments and has industrial applicability.

The invention claimed is:

1. A kinase inhibitor, comprising a compound of Formula (I), or a pharmaceutically acceptable salt, solvate, ester, or acid thereof, wherein the compound inhibits activity of wild-type KIT and/or mutant KIT kinase:

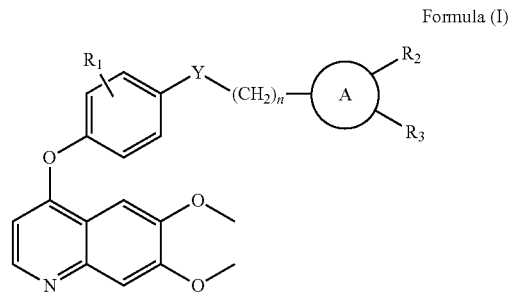

Formula (I)

wherein Y is

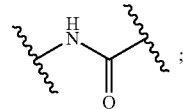 [SMILES: *NC(*)=O]

A is phenyl;

n is 1;

$R_1$ is selected from hydrogen, halo, $C_{1-6}$alkyl, $C_{1-6}$haloalkyl, $C_{1-6}$alkoxy and cyano;

each of $R_2$ and $R_3$ is independently selected from hydrogen, halo, $C_{1-6}$alkyl, $C_{1-6}$haloalkyl, $C_{1-6}$alkoxy, or $R_2$ and $R_3$ together form a phenyl or 5-membered heterocyclyl.

2. The kinase inhibitor of claim 1, wherein $R_1$ is selected from hydrogen, fluoro, chloro, methyl, ethyl, propyl, or cyano; each of $R_2$ and $R_3$ is independently selected from hydrogen, fluoro, chloro, methyl, ethyl, propyl, trifluoromethyl, difluoromethyl, trifluoroethyl, methoxy, ethoxy, propoxy, or $R_2$ and $R_3$ together form a phenyl or dioxolane.

3. The kinase inhibitor of claim 1, comprising a compound of Formula (Ia), or a pharmaceutically acceptable salt, solvate, ester, or acid thereof:

Formula (Ia)
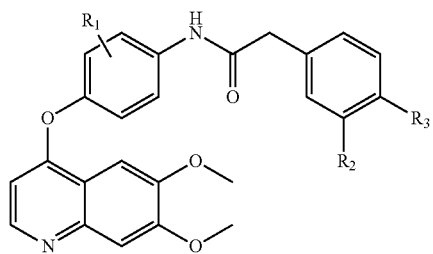
wherein $R_1$ is selected from hydrogen, fluoro, chloro, and methyl; each of $R_2$ and $R_3$ is independently selected from hydrogen, fluoro, chloro, methyl, and trifluoromethyl, or $R_2$ and $R_3$ together form a phenyl.
4. The kinase inhibitor of claim 1, comprising a compound listed below or a pharmaceutically acceptable salt, solvate, ester, or acid thereof:
1
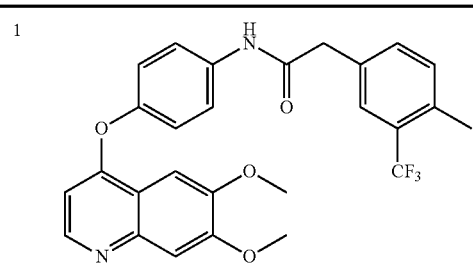
2
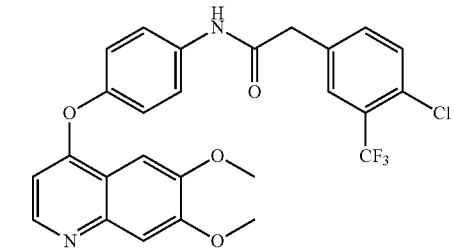
3
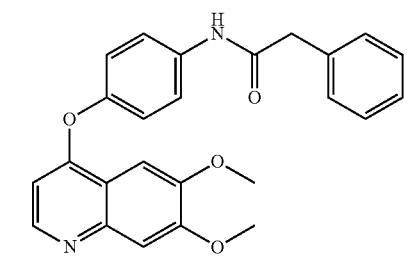 [SMILES: COc1cc2nccc(Oc3ccc(NC(=O)Cc4ccccc4)cc3)c2cc1OC]
5
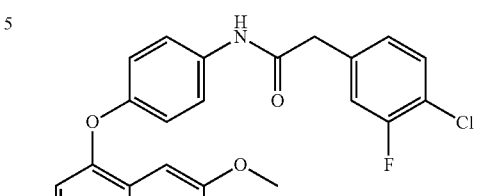
6
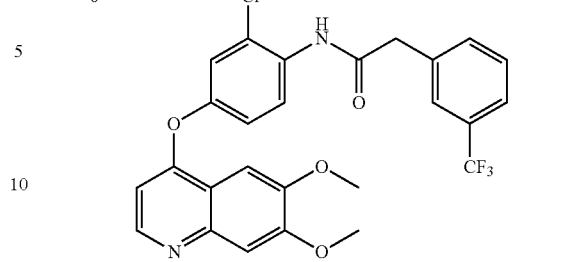
7
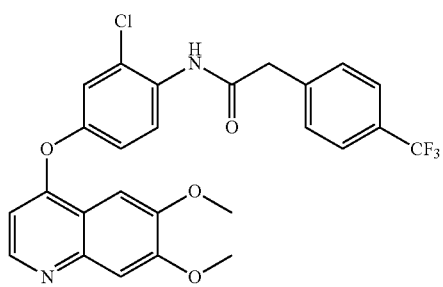 [SMILES: COc1cc2nccc(Oc3ccc(NC(=O)Cc4ccc(C(F)(F)F)cc4)c(Cl)c3)c2cc1OC]
8
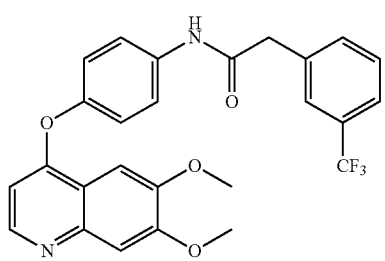 [SMILES: COc1cc2nccc(Oc3ccc(NC(=O)Cc4cccc(C(F)(F)F)c4)cc3)c2cc1OC]
9
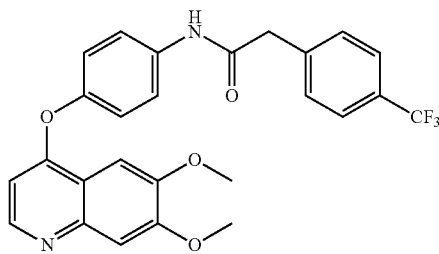 [SMILES: COc1cc2nccc(Oc3ccc(NC(=O)Cc4ccc(C(F)(F)F)cc4)cc3)c2cc1OC]
10
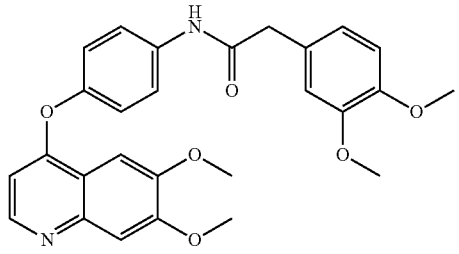 [SMILES: COc1ccc(CC(=O)Nc2ccc(Oc3ccnc4cc(OC)c(OC)cc34)cc2)cc1OC]
11
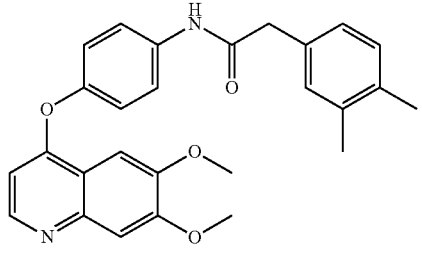 [SMILES: COc1cc2nccc(Oc3ccc(NC(=O)Cc4ccc(C)c(C)c4)cc3)c2cc1OC]

| | | | |
|---|---|---|---|
| 12 | 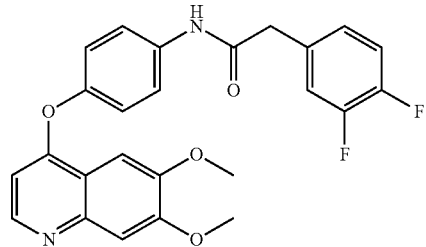 [SMILES: COc1cc2nccc(Oc3ccc(NC(=O)Cc4ccc(F)c(F)c4)cc3)c2cc1OC] | 18 | 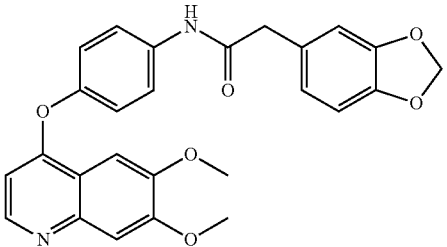 |
| 13 | 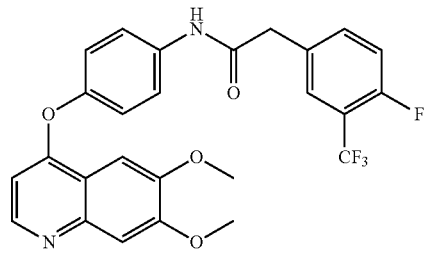 [SMILES: COc1cc2nccc(Oc3ccc(NC(=O)Cc4ccc(F)c(C(F)(F)F)c4)cc3)c2cc1OC] | 19 | 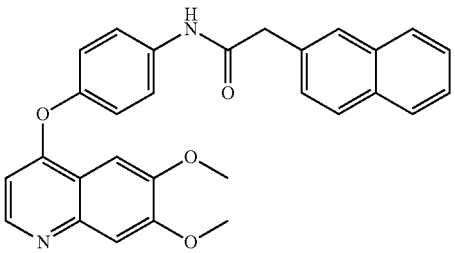 |
| 14 | 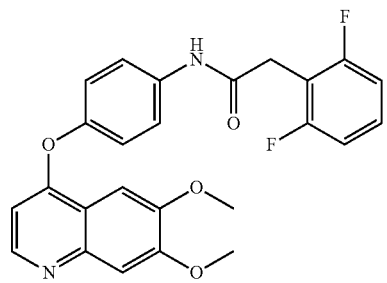 [SMILES: COc1cc2nccc(Oc3ccc(NC(=O)Cc4c(F)cccc4F)cc3)c2cc1OC] | 20 | 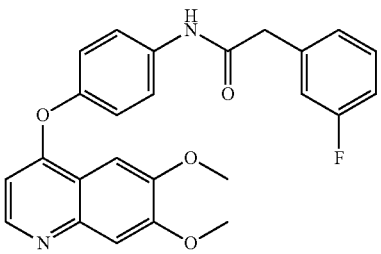 |
| 15 | 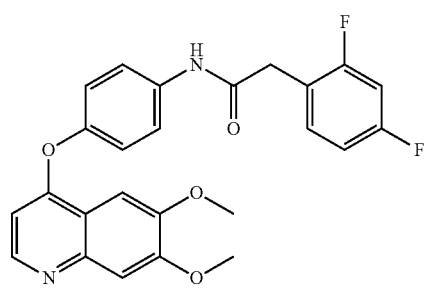 [SMILES: COc1cc2nccc(Oc3ccc(NC(=O)Cc4ccc(F)cc4F)cc3)c2cc1OC] | 23 | 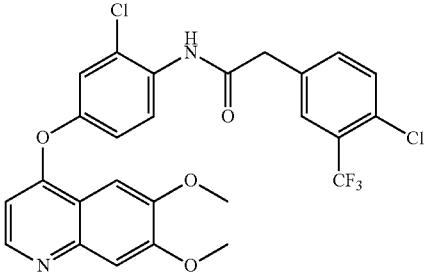 |
| 16 | 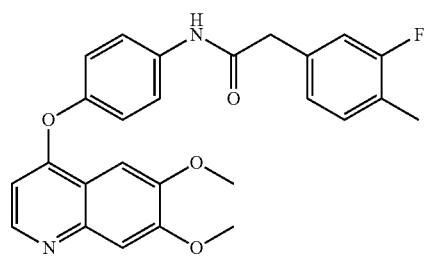 [SMILES: COc1cc2nccc(Oc3ccc(NC(=O)Cc4ccc(C)c(F)c4)cc3)c2cc1OC] | 24 | 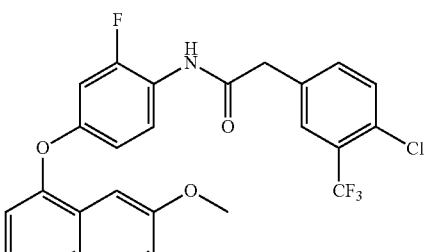 |
| 17 | 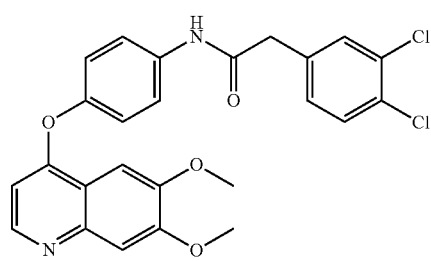 [SMILES: COc1cc2nccc(Oc3ccc(NC(=O)Cc4ccc(Cl)c(Cl)c4)cc3)c2cc1OC] | 25 | 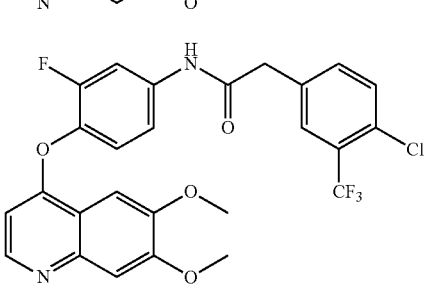 |

26 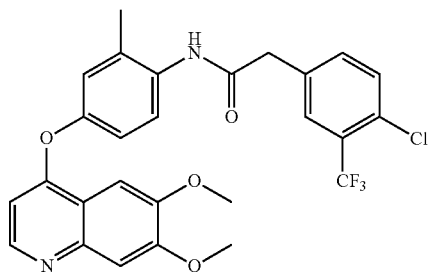 [SMILES: COc1cc2nccc(Oc3ccc(NC(=O)Cc4ccc(Cl)c(C(F)(F)F)c4)c(C)c3)c2cc1OC]

27 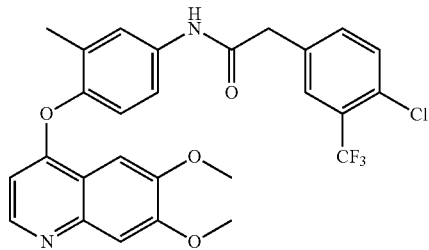

36 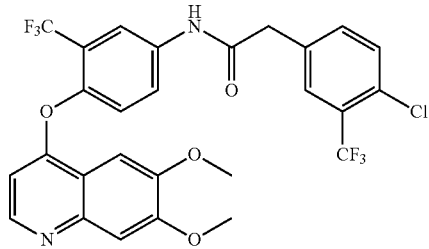

37 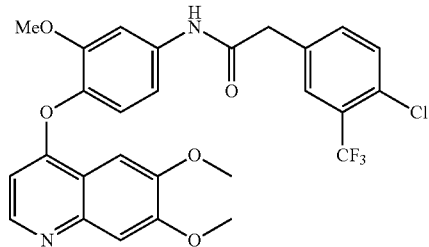

38 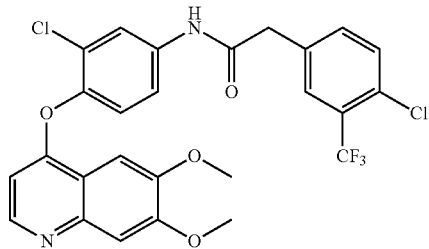

39 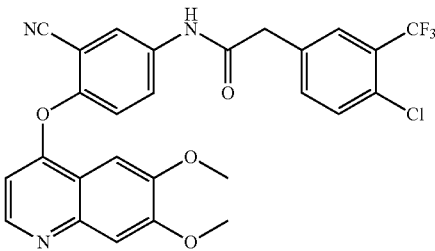 [SMILES: COc1cc2nccc(Oc3ccc(NC(=O)Cc4ccc(Cl)c(C(F)(F)F)c4)cc3C#N)c2cc1OC]

40 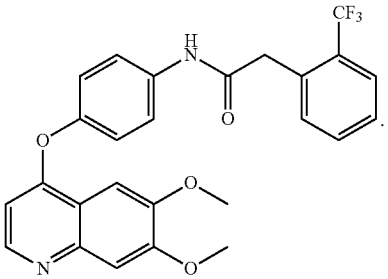 [SMILES: COc1cc2nccc(Oc3ccc(NC(=O)Cc4ccccc4C(F)(F)F)cc3)c2cc1OC]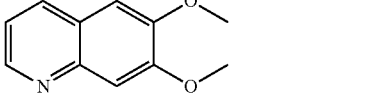

5. A pharmaceutical composition, comprising the compound or the pharmaceutically acceptable salt, solvate, ester, or acid thereof according to claim 1 and a pharmaceutically acceptable carrier or excipient as well as optionally other therapeutic agents.

6. A method for inhibiting activity of wild-type KIT and/or mutant KIT tyrosine kinase in a subject, wherein the method comprises administering the compound or the pharmaceutically acceptable salt, solvate, ester, or acid thereof according to claim 1 to the subject.

7. A method for treatment or amelioration of diseases, disorders or conditions that are modulated or affected by activity of wild-type KIT and/or mutant KIT kinase or in which activity of wild-type KIT and/or mutant KIT kinase is implicated in a subject, wherein the method comprises administering the compound or the pharmaceutically acceptable salt, solvate, ester, or acid thereof according to claim 1 to the subject, wherein the diseases, disorders or conditions are selected from the following proliferative diseases: gastrointestinal stromal tumor, colorectal cancer, acute myeloblastic leukemia, chronic myelogenous leukemia, systemic mastocytosis, fibrosis, seminoma, dysgerminoma, lung cancer, melanoma, breast cancer, neuroblastoma, non-Hodgkin's lymphoma, colon cancer, ovarian cancer, prostate cancer, pancreatic cancer, cervical cancer, multiple myeloma, neck and head tumors, or a combination thereof.

8. The method according to claim 7, wherein the diseases, disorders or conditions are gastrointestinal stromal tumor associated with KIT mutation.

* * * * *